United States Patent
Jimenez, Jr. et al.

(10) Patent No.: US 9,675,486 B2
(45) Date of Patent: Jun. 13, 2017

(54) STENT DELIVERY SYSTEM

(71) Applicant: C. R. Bard, Inc., Murray Hill, NJ (US)

(72) Inventors: Teodoro S. Jimenez, Jr., Irvine, CA (US); John Fulkerson, Rancho Santa Margarita, CA (US); Raffaele Mazzei, Encinitas, CA (US)

(73) Assignee: C.R. Bard, Inc., Murray Hill, NJ (US)

( * ) Notice: Subject to any disclaimer, the term of this patent is extended or adjusted under 35 U.S.C. 154(b) by 48 days.

(21) Appl. No.: 14/333,851

(22) Filed: Jul. 17, 2014

(65) Prior Publication Data

US 2014/0330362 A1 Nov. 6, 2014

Related U.S. Application Data

(63) Continuation of application No. 11/652,737, filed on Jan. 12, 2007, now Pat. No. 8,808,346.

(60) Provisional application No. 60/789,734, filed on Apr. 5, 2006, provisional application No. 60/759,136, filed on Jan. 13, 2006.

(51) Int. Cl.
*A61F 2/966* (2013.01)
*A61F 2/95* (2013.01)

(52) U.S. Cl.
CPC ............... *A61F 2/966* (2013.01); *A61F 2/95* (2013.01); *A61F 2002/9517* (2013.01)

(58) Field of Classification Search
CPC .... A61F 2/95; A61F 2/966; A61F 2002/9517; A61F 2002/011; A61F 2/962
See application file for complete search history.

(56) References Cited

U.S. PATENT DOCUMENTS

| | | | |
|---|---|---|---|
| 1,988,060 | A | 1/1935 | Vollenbroich |
| 2,934,211 | A | 4/1960 | Shivek |
| 2,939,680 | A | 6/1960 | Powell |
| 3,070,057 | A | 12/1962 | Dezzani |
| 3,562,427 | A | 2/1971 | Yano et al. |
| 3,585,707 | A | 6/1971 | Stevens |
| 3,871,382 | A | 3/1975 | Mann |
| 3,881,423 | A | 5/1975 | Woods et al. |
| 4,256,113 | A | 3/1981 | Chamness |
| 4,553,545 | A | 11/1985 | Maass et al. |
| 4,580,568 | A | 4/1986 | Gianturco |
| 4,616,648 | A | 10/1986 | Simpson |
| 4,649,922 | A | 3/1987 | Wiktor |

(Continued)

FOREIGN PATENT DOCUMENTS

| | | |
|---|---|---|
| CA | 2155527 A1 | 8/1994 |
| DE | 1775056 A1 | 3/1972 |

(Continued)

OTHER PUBLICATIONS

U.S. Appl. No. 11/652,737, filed Jan. 12, 2007 Non-Final Office Action dated Apr. 12, 2013.

(Continued)

*Primary Examiner* — Thomas McEvoy
(74) *Attorney, Agent, or Firm* — C.R. Bard Intellectual Property Buchalter

(57) ABSTRACT

One preferred embodiment includes a stent delivery system including a retractable sheath and an outer stability sheath. The stability sheath freely rotates relative to the retractable sheath, relieving compression forces caused by twisting of stability sheath in when in a tortuous conformation.

3 Claims, 24 Drawing Sheets

(56) References Cited

U.S. PATENT DOCUMENTS

| | | | |
|---|---|---|---|
| 4,665,918 A | 5/1987 | Garza et al. |
| 4,723,547 A | 2/1988 | Kullas et al. |
| 4,733,665 A | 3/1988 | Palmaz |
| 4,739,762 A | 4/1988 | Palmaz |
| 4,748,982 A | 6/1988 | Horzewski et al. |
| 4,760,622 A | 8/1988 | Rohrman |
| 4,771,773 A | 9/1988 | Kropf |
| 4,800,882 A | 1/1989 | Gianturco |
| 4,856,516 A | 8/1989 | Hillstead |
| 4,886,062 A | 12/1989 | Wiktor |
| 4,889,112 A | 12/1989 | Schachner et al. |
| 4,913,141 A | 4/1990 | Hillstead |
| 4,913,683 A | 4/1990 | Gregory |
| 4,921,483 A | 5/1990 | Wijay et al. |
| 4,969,458 A | 11/1990 | Wiktor |
| 4,990,151 A | 2/1991 | Wallsten |
| 5,019,090 A | 5/1991 | Pinchuk |
| 5,026,377 A | 6/1991 | Burton et al. |
| 5,045,072 A | 9/1991 | Castillo et al. |
| 5,049,128 A | 9/1991 | Duquette |
| 5,054,162 A | 10/1991 | Rogers |
| 5,102,417 A | 4/1992 | Palmaz |
| 5,104,404 A | 4/1992 | Wolff |
| 5,116,365 A | 5/1992 | Hillstead |
| 5,133,732 A | 7/1992 | Wiktor |
| 5,135,536 A | 8/1992 | Hillstead |
| 5,161,547 A | 11/1992 | Tower |
| 5,163,941 A | 11/1992 | Garth et al. |
| 5,190,552 A | 3/1993 | Kelman |
| 5,201,757 A | 4/1993 | Heyn et al. |
| 5,203,774 A | 4/1993 | Gilson et al. |
| 5,209,754 A | 5/1993 | Ahluwalia |
| 5,224,939 A | 7/1993 | Holman et al. |
| 5,228,452 A | 7/1993 | Samson |
| 5,242,423 A | 9/1993 | Goodsir et al. |
| 5,254,107 A | 10/1993 | Soltesz |
| 5,275,622 A | 1/1994 | Lazarus et al. |
| 5,279,596 A | 1/1994 | Castaneda et al. |
| 5,282,824 A | 2/1994 | Gianturco |
| 5,290,295 A | 3/1994 | Querals et al. |
| 5,290,310 A | 3/1994 | Makower et al. |
| 5,292,331 A | 3/1994 | Boneau |
| 5,312,351 A | 5/1994 | Gerrone |
| 5,312,363 A | 5/1994 | Ryan et al. |
| 5,334,147 A | 8/1994 | Johnson |
| 5,336,192 A | 8/1994 | Palestrant |
| 5,346,498 A | 9/1994 | Greelis et al. |
| 5,370,655 A | 12/1994 | Burns |
| 5,380,283 A | 1/1995 | Johnson |
| 5,383,892 A | 1/1995 | Cardon et al. |
| 5,387,235 A | 2/1995 | Chuter |
| 5,391,172 A | 2/1995 | Williams et al. |
| 5,399,164 A | 3/1995 | Snoke et al. |
| 5,405,378 A | 4/1995 | Strecker et al. |
| 5,411,507 A | 5/1995 | Heckele |
| 5,415,664 A | 5/1995 | Pinchuk |
| 5,417,708 A | 5/1995 | Hall et al. |
| 5,421,955 A | 6/1995 | Lau et al. |
| 5,433,723 A | 7/1995 | Lindenberg et al. |
| 5,443,477 A | 8/1995 | Marin et al. |
| 5,445,646 A | 8/1995 | Euteneuer et al. |
| 5,449,366 A | 9/1995 | Li |
| 5,449,373 A | 9/1995 | Pinchasik et al. |
| 5,456,694 A | 10/1995 | Marin et al. |
| 5,456,713 A | 10/1995 | Chuter |
| 5,458,615 A | 10/1995 | Klemm et al. |
| 5,466,221 A | 11/1995 | Zadini et al. |
| 5,470,315 A | 11/1995 | Adams |
| 5,477,856 A | 12/1995 | Lundquist |
| 5,480,423 A | 1/1996 | Ravenscroft et al. |
| 5,484,444 A | 1/1996 | Braunschweiler et al. |
| 5,507,751 A | 4/1996 | Goode et al. |
| 5,507,768 A | 4/1996 | Lau et al. |
| 5,507,769 A | 4/1996 | Marin et al. |
| 5,509,900 A | 4/1996 | Kirkman |
| 5,514,154 A | 5/1996 | Lau et al. |
| 5,531,690 A | 7/1996 | Solar |
| 5,534,007 A * | 7/1996 | St. Germain ............ A61F 2/95 |
| | | | 606/191 |
| 5,536,248 A | 7/1996 | Weaver et al. |
| 5,538,510 A | 7/1996 | Fontirroche et al. |
| 5,542,924 A | 8/1996 | Snoke et al. |
| 5,556,389 A | 9/1996 | Liprie |
| 5,562,726 A | 10/1996 | Chuter |
| 5,562,728 A | 10/1996 | Lazarus et al. |
| 5,569,296 A | 10/1996 | Marin et al. |
| 5,571,086 A | 11/1996 | Kaplan et al. |
| 5,571,172 A | 11/1996 | Chin |
| 5,573,530 A | 11/1996 | Fleury et al. |
| 5,578,074 A | 11/1996 | Mirigian |
| 5,591,172 A | 1/1997 | Bachmann et al. |
| 5,591,196 A | 1/1997 | Marin et al. |
| 5,601,568 A | 2/1997 | Chevillon et al. |
| 5,603,721 A | 2/1997 | Lau et al. |
| 5,603,801 A | 2/1997 | DeFriese et al. |
| 5,605,530 A | 2/1997 | Fischell et al. |
| 5,609,627 A | 3/1997 | Goicoechea et al. |
| 5,618,300 A | 4/1997 | Marin et al. |
| 5,628,755 A | 5/1997 | Heller et al. |
| 5,630,801 A | 5/1997 | Roussigne et al. |
| 5,645,076 A | 7/1997 | Yoon |
| 5,649,906 A | 7/1997 | Gory et al. |
| 5,666,970 A | 9/1997 | Smith |
| 5,669,936 A | 9/1997 | Lazarus |
| 5,672,179 A | 9/1997 | Garth et al. |
| 5,674,208 A | 10/1997 | Berg et al. |
| 5,674,278 A | 10/1997 | Boneau |
| 5,681,322 A | 10/1997 | Hartigan, Jr. |
| 5,683,345 A | 11/1997 | Waksman et al. |
| 5,683,451 A | 11/1997 | Lenker et al. |
| 5,690,644 A | 11/1997 | Yurek et al. |
| 5,693,084 A | 12/1997 | Chuter |
| 5,695,498 A | 12/1997 | Tower |
| 5,695,499 A | 12/1997 | Helgerson et al. |
| 5,695,517 A | 12/1997 | Marin et al. |
| 5,697,936 A | 12/1997 | Shipko et al. |
| 5,697,949 A | 12/1997 | Giurtino et al. |
| 5,704,914 A | 1/1998 | Stocking et al. |
| 5,707,376 A | 1/1998 | Kavteladze et al. |
| 5,709,703 A | 1/1998 | Lukic et al. |
| 5,713,917 A | 2/1998 | Leonhardt et al. |
| 5,713,948 A | 2/1998 | Uflacker |
| 5,716,365 A | 2/1998 | Goicoechea et al. |
| 5,716,393 A | 2/1998 | Lindenberg et al. |
| 5,720,776 A | 2/1998 | Chuter et al. |
| 5,725,534 A | 3/1998 | Rasmussen |
| 5,728,158 A | 3/1998 | Lau et al. |
| 5,733,267 A | 3/1998 | Del Toro |
| 5,733,303 A | 3/1998 | Israel et al. |
| 5,735,893 A | 4/1998 | Lau et al. |
| 5,738,667 A | 4/1998 | Solar |
| 5,741,298 A | 4/1998 | MacLeod |
| 5,743,876 A | 4/1998 | Swanson |
| 5,749,921 A | 5/1998 | Lenker et al. |
| 5,755,777 A | 5/1998 | Chuter |
| 5,759,186 A | 6/1998 | Bachmann et al. |
| 5,766,184 A | 6/1998 | Matsuno et al. |
| 5,769,871 A | 6/1998 | Mers Kelly et al. |
| 5,776,141 A | 7/1998 | Klein et al. |
| 5,776,142 A | 7/1998 | Gunderson |
| 5,776,161 A | 7/1998 | Globerman et al. |
| 5,776,186 A | 7/1998 | Uflacker |
| 5,780,807 A | 7/1998 | Saunders |
| 5,782,855 A | 7/1998 | Lau et al. |
| 5,788,707 A | 8/1998 | Del Toro et al. |
| 5,795,325 A | 8/1998 | Valley et al. |
| 5,800,456 A | 9/1998 | Maeda et al. |
| 5,800,520 A | 9/1998 | Fogarty et al. |
| 5,807,241 A | 9/1998 | Heimberger et al. |
| 5,807,327 A | 9/1998 | Green et al. |
| 5,810,768 A | 9/1998 | Lopez |
| 5,810,837 A | 9/1998 | Hofmann et al. |
| 5,810,869 A | 9/1998 | Kaplan et al. |
| 5,810,872 A | 9/1998 | Kanesaka et al. |

(56) References Cited

U.S. PATENT DOCUMENTS

| | | |
|---|---|---|
| 5,814,062 A | 9/1998 | Sepetka et al. |
| 5,824,058 A | 10/1998 | Ravenscroft et al. |
| 5,833,694 A | 11/1998 | Poncet |
| 5,840,064 A | 11/1998 | Liprie |
| 5,843,088 A | 12/1998 | Barra et al. |
| 5,843,092 A | 12/1998 | Heller et al. |
| 5,843,120 A | 12/1998 | Israel et al. |
| 5,843,244 A | 12/1998 | Pelton et al. |
| 5,851,210 A | 12/1998 | Torossian |
| 5,860,998 A | 1/1999 | Robinson et al. |
| RE36,104 E | 2/1999 | Solar |
| 5,868,755 A | 2/1999 | Kanner et al. |
| 5,873,906 A | 2/1999 | Lau et al. |
| 5,879,382 A | 3/1999 | Boneau |
| 5,891,154 A | 4/1999 | Loeffler |
| 5,904,648 A | 5/1999 | Arndt et al. |
| 5,906,579 A | 5/1999 | Vander Salm et al. |
| 5,906,619 A | 5/1999 | Olson et al. |
| 5,910,145 A | 6/1999 | Fischell et al. |
| 5,913,897 A | 6/1999 | Corso, Jr. et al. |
| 5,919,225 A | 7/1999 | Lau et al. |
| 5,925,061 A | 7/1999 | Ogi et al. |
| 5,928,246 A | 7/1999 | Gordon et al. |
| 5,931,842 A | 8/1999 | Goldsteen et al. |
| 5,944,727 A | 8/1999 | Ahari et al. |
| 5,951,585 A | 9/1999 | Cathcart et al. |
| 5,954,729 A | 9/1999 | Bachmann et al. |
| 5,961,536 A | 10/1999 | Mickley et al. |
| 5,968,052 A | 10/1999 | Sullivan, III et al. |
| 5,968,053 A | 10/1999 | Revelas |
| 5,968,061 A | 10/1999 | Mirza |
| 5,968,068 A | 10/1999 | Dehdashtian et al. |
| 5,968,069 A | 10/1999 | Dusbabek et al. |
| 5,972,018 A | 10/1999 | Israel et al. |
| 5,980,515 A | 11/1999 | Tu |
| 5,984,225 A | 11/1999 | Enzinna |
| 5,992,000 A | 11/1999 | Humphrey et al. |
| 5,997,562 A | 12/1999 | Zadno-Azizi et al. |
| 6,004,328 A | 12/1999 | Solar |
| 6,015,429 A | 1/2000 | Lau et al. |
| 6,019,778 A | 2/2000 | Wilson et al. |
| 6,027,509 A | 2/2000 | Schatz et al. |
| 6,039,744 A | 3/2000 | Forber |
| 6,039,749 A | 3/2000 | Marin et al. |
| 6,042,597 A | 3/2000 | Kveen et al. |
| 6,045,536 A | 4/2000 | Meier et al. |
| 6,071,263 A | 6/2000 | Kirkman |
| 6,071,286 A | 6/2000 | Mawad |
| 6,077,295 A | 6/2000 | Limon et al. |
| 6,080,140 A | 6/2000 | Swaminathan et al. |
| 6,083,194 A | 7/2000 | Lopez |
| 6,090,035 A | 7/2000 | Campbell et al. |
| 6,090,063 A | 7/2000 | Makower et al. |
| 6,090,128 A | 7/2000 | Douglas |
| 6,096,009 A | 8/2000 | Windheuser et al. |
| 6,096,045 A | 8/2000 | Del Toro et al. |
| 6,096,056 A | 8/2000 | Brown |
| 6,102,890 A | 8/2000 | Stivland et al. |
| 6,102,942 A | 8/2000 | Ahari |
| 6,110,191 A | 8/2000 | Dehdashtian et al. |
| 6,113,607 A | 9/2000 | Lau et al. |
| 6,117,140 A | 9/2000 | Munsinger |
| 6,117,165 A | 9/2000 | Becker |
| 6,117,167 A | 9/2000 | Goicoechea et al. |
| 6,123,723 A | 9/2000 | Konya et al. |
| 6,129,755 A | 10/2000 | Mathis et al. |
| 6,136,007 A | 10/2000 | Goldsteen et al. |
| 6,136,572 A | 10/2000 | Benatti et al. |
| 6,143,014 A | 11/2000 | Dehdashtian et al. |
| 6,143,021 A | 11/2000 | Staehle |
| 6,146,415 A | 11/2000 | Fitz |
| 6,149,680 A | 11/2000 | Shelso et al. |
| 6,156,053 A | 12/2000 | Gandhi et al. |
| 6,156,054 A | 12/2000 | Zadno-Azizi et al. |
| 6,156,063 A | 12/2000 | Douglas |
| 6,159,228 A | 12/2000 | Frid et al. |
| 6,159,239 A | 12/2000 | Greenhalgh |
| 6,167,315 A | 12/2000 | Coe et al. |
| 6,168,610 B1 | 1/2001 | Marin et al. |
| 6,168,617 B1 | 1/2001 | Blaeser et al. |
| 6,174,327 B1 | 1/2001 | Mertens et al. |
| 6,183,509 B1 | 2/2001 | Dibie |
| 6,190,360 B1 | 2/2001 | Iancea et al. |
| 6,190,393 B1 | 2/2001 | Bevier et al. |
| 6,190,406 B1 | 2/2001 | Duerig et al. |
| 6,203,550 B1 | 3/2001 | Olson |
| 6,203,558 B1 | 3/2001 | Dusbabek et al. |
| 6,210,422 B1 | 4/2001 | Douglas |
| 6,214,026 B1 | 4/2001 | Lepak et al. |
| 6,217,585 B1 | 4/2001 | Houser et al. |
| 6,224,608 B1 | 5/2001 | Ciccolella et al. |
| 6,238,402 B1 | 5/2001 | Sullivan, III et al. |
| 6,238,415 B1 | 5/2001 | Sepetka et al. |
| 6,238,837 B1 | 5/2001 | Fan |
| 6,241,692 B1 | 6/2001 | Tu et al. |
| 6,245,100 B1 | 6/2001 | Davila et al. |
| 6,248,122 B1 | 6/2001 | Klumb et al. |
| 6,251,132 B1 | 6/2001 | Ravenscroft et al. |
| 6,254,608 B1 | 7/2001 | Solar |
| 6,264,689 B1 | 7/2001 | Colgan et al. |
| 6,270,521 B1 | 8/2001 | Fischell et al. |
| 6,273,879 B1 | 8/2001 | Keith et al. |
| 6,273,895 B1 | 8/2001 | Pinchuk et al. |
| 6,287,322 B1 | 9/2001 | Zhu et al. |
| 6,312,407 B1 | 11/2001 | Zadno-Azizi et al. |
| 6,319,262 B1 | 11/2001 | Bates et al. |
| 6,332,403 B1 | 12/2001 | Weise et al. |
| 6,342,067 B1 | 1/2002 | Mathis et al. |
| 6,344,053 B1 | 2/2002 | Boneau |
| 6,346,118 B1 | 2/2002 | Baker et al. |
| 6,348,065 B1 | 2/2002 | Brown et al. |
| 6,358,274 B1 | 3/2002 | Thompson |
| 6,368,344 B1 | 4/2002 | Fitz |
| 6,375,676 B1 | 4/2002 | Cox |
| 6,383,211 B1 | 5/2002 | Staehle |
| 6,391,050 B1 | 5/2002 | Broome |
| 6,391,051 B2 | 5/2002 | Sullivan, III et al. |
| 6,395,020 B1 | 5/2002 | Ley et al. |
| 6,402,760 B1 | 6/2002 | Fedida |
| 6,413,269 B1 | 7/2002 | Bui et al. |
| 6,425,898 B1 | 7/2002 | Wilson et al. |
| 6,443,979 B1 | 9/2002 | Stalker et al. |
| 6,443,982 B1 | 9/2002 | Israel et al. |
| 6,461,381 B2 | 10/2002 | Israel et al. |
| 6,471,673 B1 | 10/2002 | Kastenhofer |
| 6,488,703 B1 | 12/2002 | Kveen et al. |
| 6,500,248 B1 | 12/2002 | Hayashi |
| 6,514,261 B1 | 2/2003 | Randall et al. |
| 6,517,569 B2 | 2/2003 | Mikus et al. |
| 6,520,938 B1 | 2/2003 | Funderburk et al. |
| 6,520,983 B1 | 2/2003 | Colgan et al. |
| 6,527,779 B1 | 3/2003 | Rourke |
| 6,527,789 B1 | 3/2003 | Lau et al. |
| 6,569,181 B1 | 5/2003 | Burns |
| 6,572,643 B1 | 6/2003 | Gharibadeh |
| 6,575,993 B1 | 6/2003 | Yock |
| 6,582,459 B1 | 6/2003 | Lau et al. |
| 6,582,460 B1 | 6/2003 | Cryer |
| 6,599,296 B1 | 7/2003 | Gillick et al. |
| 6,613,014 B1 | 9/2003 | Chi |
| 6,613,075 B1 | 9/2003 | Healy et al. |
| 6,629,981 B2 | 10/2003 | Bui et al. |
| 6,645,238 B2 | 11/2003 | Smith |
| 6,652,506 B2 | 11/2003 | Bowe et al. |
| 6,659,977 B2 | 12/2003 | Kastenhofer |
| 6,660,031 B2 | 12/2003 | Tran et al. |
| 6,660,827 B2 | 12/2003 | Loomis et al. |
| 6,663,666 B1 | 12/2003 | Quiachon et al. |
| 6,695,862 B2 | 2/2004 | Cox et al. |
| 6,716,190 B1 | 4/2004 | Glines et al. |
| 6,716,238 B2 | 4/2004 | Elliott |
| 6,749,627 B2 | 6/2004 | Thompson et al. |
| 6,755,854 B2 | 6/2004 | Gillick et al. |
| 6,773,446 B1 | 8/2004 | Dwyer et al. |

(56) References Cited

U.S. PATENT DOCUMENTS

| | | |
|---|---|---|
| 6,786,918 B1 | 9/2004 | Krivoruchko et al. |
| 6,821,292 B2 | 11/2004 | Pazienza et al. |
| 6,866,669 B2 | 3/2005 | Buzzard et al. |
| 6,884,259 B2 | 4/2005 | Tran et al. |
| 6,911,039 B2 | 6/2005 | Shiu et al. |
| 6,913,613 B2 | 7/2005 | Schwarz et al. |
| 6,939,352 B2 | 9/2005 | Buzzard et al. |
| 6,939,370 B2 | 9/2005 | Hartley et al. |
| 7,033,368 B2 | 4/2006 | Rourke |
| 7,052,511 B2 | 5/2006 | Weldon et al. |
| 7,122,050 B2 | 10/2006 | Randall et al. |
| 7,172,617 B2 | 2/2007 | Colgan et al. |
| 7,294,135 B2 | 11/2007 | Stephens et al. |
| 7,323,006 B2 | 1/2008 | Andreas et al. |
| 7,381,216 B2 | 6/2008 | Buzzard et al. |
| D576,725 S | 9/2008 | Shumer et al. |
| D578,216 S | 10/2008 | Dorn et al. |
| D578,643 S | 10/2008 | Shumer et al. |
| D578,644 S | 10/2008 | Shumer et al. |
| D578,645 S | 10/2008 | Shumer et al. |
| 7,506,650 B2 | 3/2009 | Lowe et al. |
| 7,550,001 B2 | 6/2009 | Dorn et al. |
| 7,553,322 B2 | 6/2009 | Dorn et al. |
| D598,543 S | 8/2009 | Vogel et al. |
| 7,582,054 B2 | 9/2009 | Okada |
| 7,935,141 B2 | 5/2011 | Randall et al. |
| 8,062,344 B2 | 11/2011 | Dorn et al. |
| 8,075,606 B2 | 12/2011 | Dorn |
| 8,382,813 B2 | 2/2013 | Shumer |
| 8,419,784 B2 | 4/2013 | Matsuoka et al. |
| 8,500,789 B2 | 8/2013 | Wuebbeling et al. |
| 2001/0007082 A1 | 7/2001 | Dusbabek et al. |
| 2001/0044621 A1 | 11/2001 | Klumb et al. |
| 2001/0051822 A1 | 12/2001 | Stack et al. |
| 2002/0004663 A1 | 1/2002 | Gittings et al. |
| 2002/0035394 A1 | 3/2002 | Fierens et al. |
| 2002/0045929 A1 | 4/2002 | Diaz |
| 2002/0052642 A1 | 5/2002 | Cox et al. |
| 2002/0116044 A1 | 8/2002 | Cottone et al. |
| 2002/0151955 A1 | 10/2002 | Tran et al. |
| 2002/0183827 A1 | 12/2002 | Derus et al. |
| 2002/0188341 A1 | 12/2002 | Elliott |
| 2003/0028236 A1 | 2/2003 | Gillick et al. |
| 2003/0049295 A1 | 3/2003 | Guggenbichler et al. |
| 2003/0050686 A1 | 3/2003 | Raeder-Devens et al. |
| 2003/0074043 A1 | 4/2003 | Thompson |
| 2003/0074045 A1 | 4/2003 | Buzzard et al. |
| 2003/0105451 A1 | 6/2003 | Westlund et al. |
| 2003/0135162 A1 | 7/2003 | Deyette et al. |
| 2003/0163085 A1 | 8/2003 | Tanner et al. |
| 2003/0167060 A1 | 9/2003 | Buzzard et al. |
| 2003/0191516 A1 | 10/2003 | Weldon et al. |
| 2003/0208262 A1 | 11/2003 | Gaber |
| 2004/0006380 A1 | 1/2004 | Buck et al. |
| 2004/0098079 A1 | 5/2004 | Hartley et al. |
| 2004/0098083 A1 | 5/2004 | Tran et al. |
| 2004/0143160 A1 | 7/2004 | Couvillon |
| 2004/0148009 A1 | 7/2004 | Buzzard et al. |
| 2004/0153137 A1 | 8/2004 | Gaschino et al. |
| 2004/0186547 A1 | 9/2004 | Dorn et al. |
| 2004/0193180 A1 | 9/2004 | Buzzard et al. |
| 2004/0193283 A1 | 9/2004 | Rioux et al. |
| 2005/0004515 A1 | 1/2005 | Hart et al. |
| 2005/0021123 A1 | 1/2005 | Dorn et al. |
| 2005/0027306 A1 | 2/2005 | Krivoruchko et al. |
| 2005/0027345 A1 | 2/2005 | Horan et al. |
| 2005/0033402 A1 | 2/2005 | Cully et al. |
| 2005/0043618 A1 | 2/2005 | Mansouri-Ruiz |
| 2005/0043713 A1 | 2/2005 | Zhou |
| 2005/0060016 A1 | 3/2005 | Wu et al. |
| 2005/0080476 A1 | 4/2005 | Gunderson et al. |
| 2005/0085851 A1 | 4/2005 | Fiehler et al. |
| 2005/0090890 A1 | 4/2005 | Wu et al. |
| 2005/0149159 A1 | 7/2005 | Andreas et al. |
| 2005/0159725 A1 | 7/2005 | Tockman et al. |
| 2005/0182475 A1 | 8/2005 | Jen et al. |
| 2005/0209670 A1 | 9/2005 | George et al. |
| 2005/0209672 A1 | 9/2005 | George et al. |
| 2005/0209674 A1 | 9/2005 | Kutscher et al. |
| 2005/0240254 A1 | 10/2005 | Austin |
| 2005/0256562 A1 | 11/2005 | Clerc et al. |
| 2005/0273151 A1 | 12/2005 | Fulkerson et al. |
| 2005/0288764 A1 | 12/2005 | Snow et al. |
| 2006/0058866 A1 | 3/2006 | Cully et al. |
| 2006/0074477 A1 | 4/2006 | Berthiaume et al. |
| 2006/0085057 A1 | 4/2006 | George et al. |
| 2006/0095116 A1 | 5/2006 | Bolduc et al. |
| 2006/0100686 A1 | 5/2006 | Bolduc et al. |
| 2006/0167467 A1 | 7/2006 | Rourke |
| 2006/0241737 A1 | 10/2006 | Tockman et al. |
| 2006/0259124 A1 | 11/2006 | Matsuoka et al. |
| 2006/0276873 A1 | 12/2006 | Sato |
| 2007/0016164 A1 | 1/2007 | Dudney et al. |
| 2007/0050006 A1 | 3/2007 | Lavelle |
| 2007/0055339 A1 | 3/2007 | George et al. |
| 2007/0055342 A1 | 3/2007 | Wu et al. |
| 2007/0060999 A1 | 3/2007 | Randall et al. |
| 2007/0073379 A1 | 3/2007 | Chang |
| 2007/0073389 A1 | 3/2007 | Bolduc et al. |
| 2007/0088421 A1 | 4/2007 | Loewen |
| 2007/0100420 A1 | 5/2007 | Kavanagh et al. |
| 2007/0100422 A1 | 5/2007 | Shumer et al. |
| 2007/0100429 A1 | 5/2007 | Wu et al. |
| 2007/0112409 A1 | 5/2007 | Wu et al. |
| 2007/0118201 A1 | 5/2007 | Pappas et al. |
| 2007/0118206 A1 | 5/2007 | Colgan et al. |
| 2007/0156222 A1 | 7/2007 | Feller et al. |
| 2007/0156224 A1 | 7/2007 | Cioanta et al. |
| 2007/0168014 A1 | 7/2007 | Jimenez et al. |
| 2007/0191864 A1 | 8/2007 | Shumer |
| 2007/0191865 A1 | 8/2007 | Pappas |
| 2007/0191925 A1 | 8/2007 | Dorn |
| 2007/0194483 A1 | 8/2007 | Guggenbichler et al. |
| 2007/0233222 A1 | 10/2007 | Roeder et al. |
| 2007/0244540 A1 | 10/2007 | Pryor |
| 2007/0255390 A1 | 11/2007 | Ducke et al. |
| 2009/0024133 A1 | 1/2009 | Keady et al. |
| 2009/0099638 A1 | 4/2009 | Grewe |
| 2010/0004606 A1 | 1/2010 | Hansen et al. |
| 2010/0036472 A1 | 2/2010 | Papp |
| 2010/0094399 A1 | 4/2010 | Dorn et al. |
| 2010/0168756 A1 | 7/2010 | Dorn et al. |
| 2010/0174290 A1 | 7/2010 | Wuebbeling et al. |
| 2013/0317592 A1 | 11/2013 | Wubbeling et al. |

FOREIGN PATENT DOCUMENTS

| | | |
|---|---|---|
| DE | 02544371 A1 | 4/1976 |
| DE | 03132323 A1 | 4/1983 |
| DE | 3219629 A1 | 12/1983 |
| DE | 4133696 A1 | 4/1993 |
| DE | 04420142 A1 | 12/1995 |
| DE | 29516712 U1 | 12/1995 |
| DE | 19539449 A1 | 4/1997 |
| DE | 29717110 U1 | 11/1997 |
| DE | 29816878 U1 | 12/1998 |
| DE | 29522101 | 12/1999 |
| DE | 19921530 | 6/2000 |
| DE | 19901530 A1 | 7/2000 |
| DE | 19936059 A1 | 2/2001 |
| DE | 20000659 U1 | 5/2001 |
| DE | 69521346 T2 | 4/2002 |
| EP | 0436303 A1 | 7/1991 |
| EP | 0505686 A1 | 9/1992 |
| EP | 0518838 A1 | 12/1992 |
| EP | 0564894 A1 | 10/1993 |
| EP | 0611556 A1 | 8/1994 |
| EP | 0630657 A1 | 12/1994 |
| EP | 0633756 B1 | 1/1995 |
| EP | 0688545 A1 | 12/1995 |
| EP | 0699451 A2 | 3/1996 |
| EP | 0712614 A1 | 5/1996 |
| EP | 0744930 A1 | 12/1996 |
| EP | 0747021 A2 | 12/1996 |

(56) References Cited

FOREIGN PATENT DOCUMENTS

| | | |
|---|---|---|
| EP | 0752896 B1 | 1/1997 |
| EP | 0790041 A2 | 8/1997 |
| EP | 0792627 A2 | 9/1997 |
| EP | 0873733 A1 | 10/1998 |
| EP | 0876804 A1 | 11/1998 |
| EP | 0947212 A2 | 10/1999 |
| EP | 1025813 A2 | 8/2000 |
| EP | 1078611 A1 | 2/2001 |
| EP | 1095634 A2 | 5/2001 |
| EP | 1117341 A1 | 7/2001 |
| EP | 1132058 A1 | 9/2001 |
| EP | 1155664 A2 | 11/2001 |
| EP | 1181906 A2 | 2/2002 |
| EP | 1199051 A2 | 4/2002 |
| EP | 1290989 A2 | 3/2003 |
| EP | 1299050 B1 | 4/2003 |
| EP | 1302178 A2 | 4/2003 |
| EP | 1383446 A1 | 1/2004 |
| EP | 1440671 A2 | 7/2004 |
| EP | 1447057 A1 | 8/2004 |
| EP | 1447058 A1 | 8/2004 |
| EP | 1637092 A2 | 3/2006 |
| FR | 2760351 A1 | 9/1998 |
| FR | 2797761 A1 | 3/2001 |
| JP | 2003518406 A | 6/2003 |
| JP | 2004147812 A | 5/2004 |
| JP | 2005530558 A | 10/2005 |
| JP | 2005532100 A | 10/2005 |
| JP | 2007-097620 A | 4/2007 |
| JP | 2007-508045 A | 4/2007 |
| MX | 303207 | 12/2012 |
| WO | 9521593 A1 | 8/1995 |
| WO | 9526775 A1 | 10/1995 |
| WO | 9618359 A1 | 6/1996 |
| WO | 9618361 A1 | 6/1996 |
| WO | 9809584 A1 | 3/1998 |
| WO | 9820811 A1 | 5/1998 |
| WO | 9823241 A2 | 6/1998 |
| WO | 9830173 A1 | 7/1998 |
| WO | 9852496 A1 | 11/1998 |
| WO | 9904728 A1 | 2/1999 |
| WO | 9925280 A1 | 5/1999 |
| WO | 9944541 A1 | 9/1999 |
| WO | 9947075 A1 | 9/1999 |
| WO | 9951167 A2 | 10/1999 |
| WO | 0000104 A1 | 1/2000 |
| WO | 0002503 A1 | 1/2000 |
| WO | 0016718 A1 | 3/2000 |
| WO | 0018330 A1 | 4/2000 |
| WO | 0067675 A1 | 11/2000 |
| WO | 0069368 A2 | 11/2000 |
| WO | 0071059 A1 | 11/2000 |
| WO | 0078246 A2 | 12/2000 |
| WO | 0078248 A1 | 12/2000 |
| WO | 0132102 A1 | 5/2001 |
| WO | 0134061 A1 | 5/2001 |
| WO | 0147436 A2 | 7/2001 |
| WO | 0158387 A1 | 8/2001 |
| WO | 0189421 | 11/2001 |
| WO | 0203888 A2 | 1/2002 |
| WO | 0203889 A2 | 1/2002 |
| WO | 02066094 A2 | 8/2002 |
| WO | 02083036 A2 | 10/2002 |
| WO | 02087470 A1 | 11/2002 |
| WO | 02102279 A2 | 12/2002 |
| WO | 03002020 A2 | 1/2003 |
| WO | 03003926 A1 | 1/2003 |
| WO | 03061724 A2 | 7/2003 |
| WO | 2004004597 A2 | 1/2004 |
| WO | 2005039448 A1 | 5/2005 |
| WO | 2005053574 A2 | 6/2005 |
| WO | 2005062980 A2 | 7/2005 |
| WO | 2005065200 A2 | 7/2005 |
| WO | 2005117759 A2 | 12/2005 |
| WO | 2006071915 A2 | 7/2006 |
| WO | 2006104143 A1 | 10/2006 |
| WO | 2007002713 A2 | 1/2007 |
| WO | 2007005799 A1 | 1/2007 |
| WO | 2007022395 A1 | 2/2007 |
| WO | 2007029242 A1 | 3/2007 |
| WO | 2007044929 A1 | 4/2007 |
| WO | 2007083470 A1 | 7/2007 |
| WO | 2008034793 A1 | 3/2008 |
| WO | 2010027998 A1 | 3/2010 |

OTHER PUBLICATIONS

U.S. Appl. No. 11/652,737, filed Jan. 12, 2007 Non-Final Office Action dated Feb. 12, 2014.
U.S. Appl. No. 11/652,737, filed Jan. 12, 2007 Advisory Action dated Dec. 30, 2013.
U.S. Appl. No. 11/652,737, filed Jan. 12, 2007 Final Office Action dated Oct. 22, 2013.
U.S. Appl. No. 11/652,737, filed Jan. 12, 2007 Notice of Allowance dated Apr. 25, 2014.
U.S. Appl. No. 12/376,670, filed Feb. 6, 2009 Final Office Action dated Dec. 17, 2013.
U.S. Appl. No. 12/376,670, filed Feb. 6, 2009 Non-Final Office Action dated Jun. 21, 2012.
U.S. Appl. No. 12/640,956, filed Dec. 17, 2009 Non-Final Office Action dated Jan. 24, 2011.
U.S. Appl. No. 12/640,956, filed Dec. 17, 2009 Notice of Allowancwe dated Jul. 13, 2011.
U.S. Appl. No. 12/668,613, filed Feb. 19, 2010 Non-Final Office Action dated Nov. 26, 2012.
"Medtronic Announces FDA Clearance of Bridge SE Biliary Stent." Business Wire, Oct. 15, 2001. www.medtronic.com/newsroom/news_20011015a.html.
"Summary for the Bridge SE Biliary Self-Expanding Stent Delivery System" Jan. 14, 2002 FDA Section 510 (k) review.
Bridge™ SE Binary Stent System, <<http:/www.medtronicave/com/includes/content/phsycians/bridges/htm>>, 3 pages, last accessed Oct. 2002.
EP 10001359.8 filed Aug. 16, 2006 European Search Report dated May 28, 2010.
EP 13170019.7 extended European Search Report dated Aug. 5, 2013.
EP 14151266.5 extended European Search Report dated Apr. 9, 2014.
JP 2008-550429 filed Jun. 27, 2008 Final Notice of Reason for Rejection dated Oct. 25, 2012.
JP 2008-550429 filed Jun. 27, 2008 Office Action dated Jan. 4, 2012.
JP 2010-515514 Notice of Reason for Rejection dated Dec. 20, 2012.
JP 2013-011060 first Official Action dated Feb. 21, 2014.
JP 2013-089100 Official Action dated Apr. 8, 2014.
PCT/EP2002/004727 filed Apr. 29, 2002 Preliminary Examination Report dated Jan. 7, 2003.
PCT/EP2002/004727 filed Apr. 29, 2002 Search Report dated Jul. 10, 2002.
PCT/EP2002/006784 filed Jun. 19, 2002 Preliminary Examination Report dated Apr. 14, 2004.
PCT/EP2002/006784 filed Jun. 19, 2002 Search Report dated Jan. 21, 2004.
PCT/EP2007/058205 filed Aug. 7, 2007 Preliminary Report on Patentability dated Aug. 4, 2008.
PCT/EP2007/058205 filed Aug. 7, 2007 Search Report dated Nov. 30, 2007.
PCT/EP2007/058205 filed Aug. 7, 2007 Written Opinion Nov. 30, 2007.
PCT/EP2008/059040 filed Jul. 1, 2008 Search Report dated Nov. 4, 2008.
PCT/EP2008/059040 filed Jul. 10, 2008 Preliminary Report on Patentability dated Sep. 29, 2009.
PCT/EP2008/059040 filed Jul. 10, 2008 Written Opinion dated Nov. 4, 2008.
PCT/US2005/019860 filed Jun. 6, 2005 Preliminary Report on Patentability dated Dec. 4, 2006.

(56) References Cited

OTHER PUBLICATIONS

PCT/US2005/019860 filed Jun. 6, 2005 Search Report dated Dec. 15, 2005.
PCT/US2005/019860 filed Jun. 6, 2005 Written Opinion dated Dec. 15, 2005.
PCT/US2006/032228 filed Aug. 16, 2006 Preliminary Report on Patentability dated Feb. 20, 2008.
PCT/US2006/032228 filed Aug. 16, 2006 Search Report dated Jan. 19, 2007.
PCT/US2006/032228 filed Aug. 16, 2006 Written Opinion dated Jan. 19, 2007.
PCT/US2007/000834 filed Jan. 12, 2007 Preliminary Report on Patentability Jul. 15, 2008.
PCT/US2007/000834 filed Jan. 12, 2007 Search Report dated Apr. 27, 2007.
PCT/US2007/000834 filed Jan. 12, 2007 Written Opinion dated Apr. 27, 2007.
U.S. Appl. No. 10/476,351, filed May 7, 2004 Final Office Action dated Feb. 4, 2009.
U.S. Appl. No. 10/476,351, filed May 7, 2004 Final Office Action dated Oct. 21, 2008.
U.S. Appl. No. 10/476,351, filed May 7, 2004 Non-Final Office Action dated Apr. 4, 2008.
U.S. Appl. No. 10/476,351, filed May 7, 2004 Notice of Allowance dated Mar. 12, 2009.
U.S. Appl. No. 10/824,033, filed Apr. 14, 2004 Non-Final Office Action dated Jul. 17, 2009.
U.S. Appl. No. 11/144,513, filed Jun. 3, 2005 Advisory Action dated Oct. 5, 2010.
U.S. Appl. No. 11/144,513, filed Jun. 3, 2005 Final Office Action dated Jul. 13, 2010.
U.S. Appl. No. 11/144,513, filed Jun. 3, 2005 Final Office Action dated Oct. 15, 2008.
U.S. Appl. No. 11/144,513, filed Jun. 3, 2005 Final Office Action dated Oct. 20, 2009.
U.S. Appl. No. 11/144,513, filed Jun. 3, 2005 Non-Final Office Action dated Feb. 2, 2010.
U.S. Appl. No. 11/144,513, filed Jun. 3, 2005 Non-Final Office Action dated Feb. 5, 2008.
U.S. Appl. No. 11/144,513, filed Jun. 3, 2005 Non-Final Office Action dated Feb. 26, 2009.
U.S. Appl. No. 11/505,185, filed Aug. 16, 2006 Non-Final Office Action dated Mar. 31, 2010.
U.S. Appl. No. 11/505,185, filed Aug. 16, 2006 Non-Final Office Action dated Aug. 31, 2009.
U.S. Appl. No. 11/505,185, filed Aug. 16, 2006 Non-Final Office Action dated Oct. 7, 2010.
U.S. Appl. No. 11/652,737, filed Jan. 12, 2007 Advisory Action dated Aug. 27, 2010.
U.S. Appl. No. 11/652,737, filed Jan. 12, 2007 Final Office Action dated May 27, 2009.
U.S. Appl. No. 11/652,737, filed Jan. 12, 2007 Final Office Action dated Jun. 10, 2010.
U.S. Appl. No. 11/652,737, filed Jan. 12, 2007 Non-Final Office Action dated Oct. 27, 2009.
U.S. Appl. No. 11/652,737, filed Jan. 12, 2007 Non-Final Office Action dated Nov. 12, 2008.

* cited by examiner

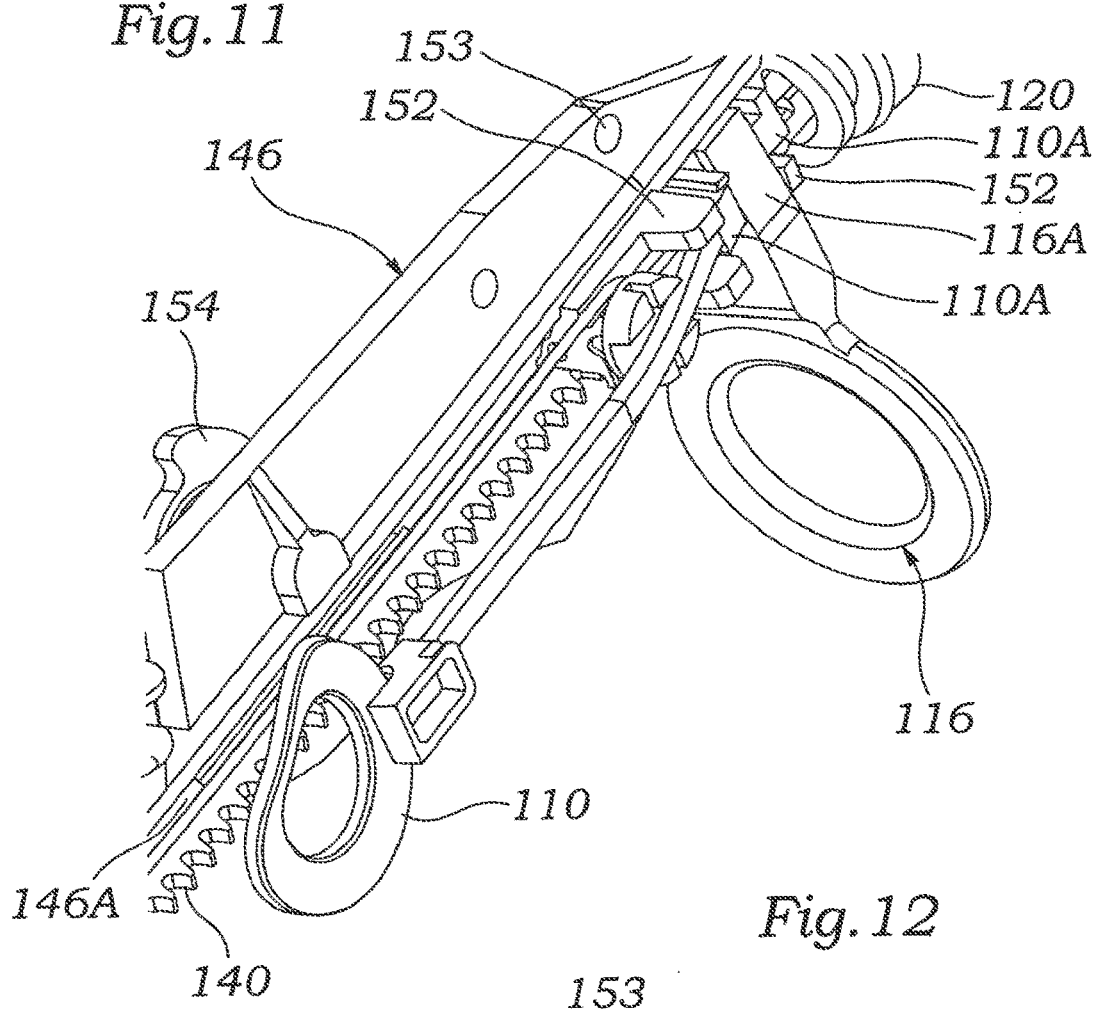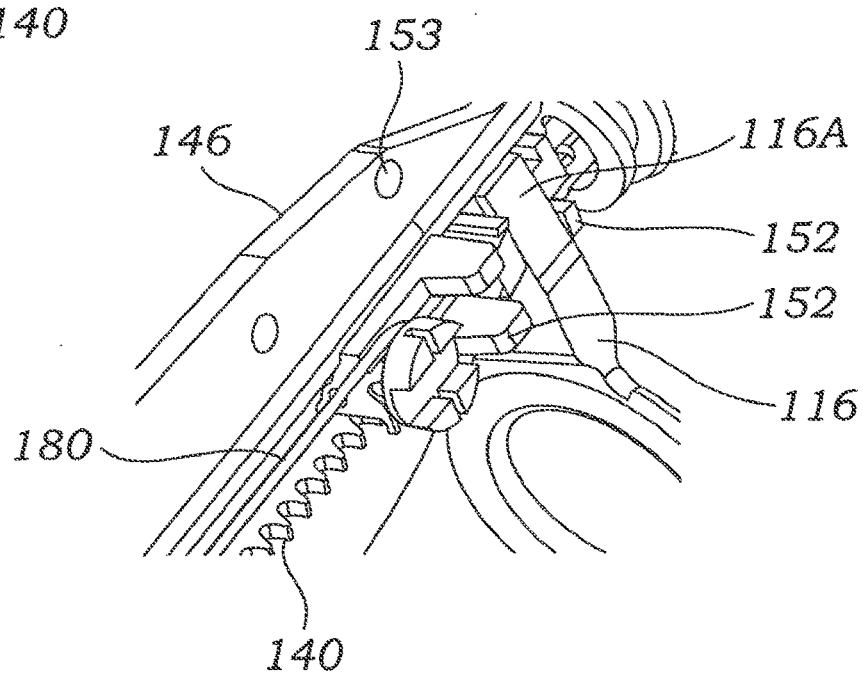

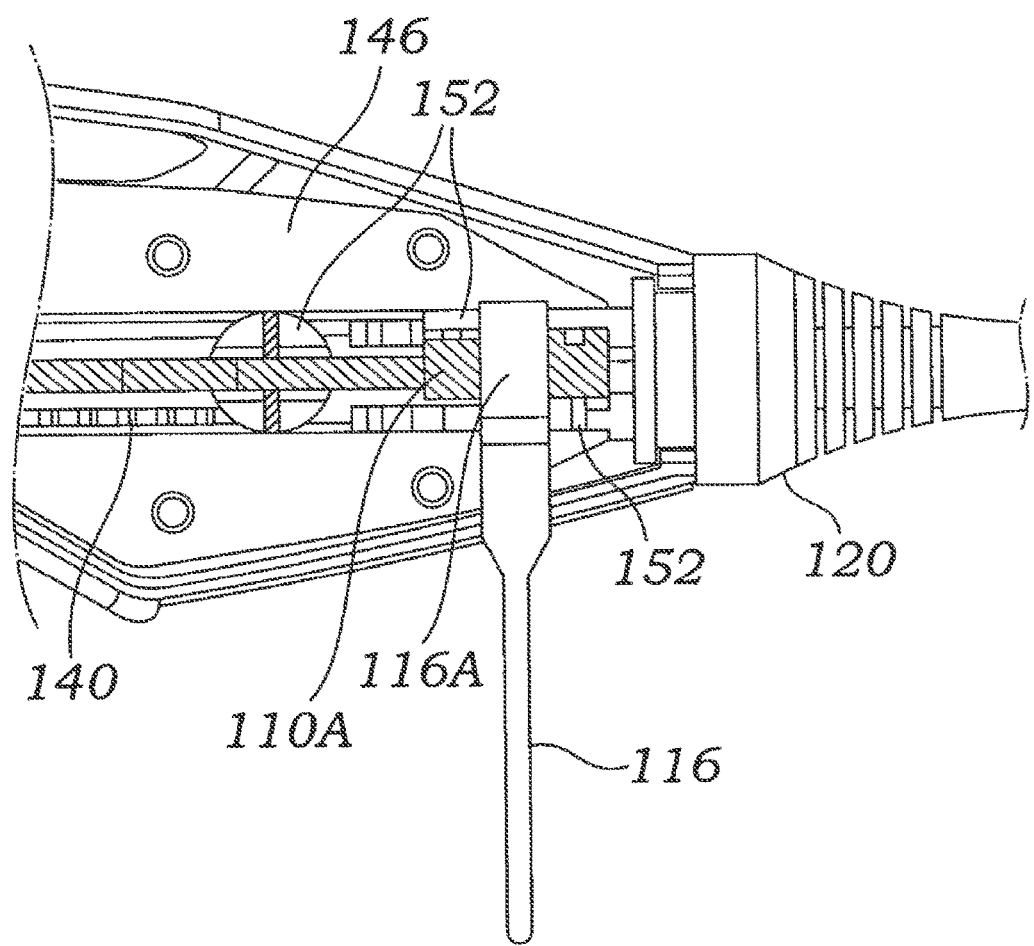

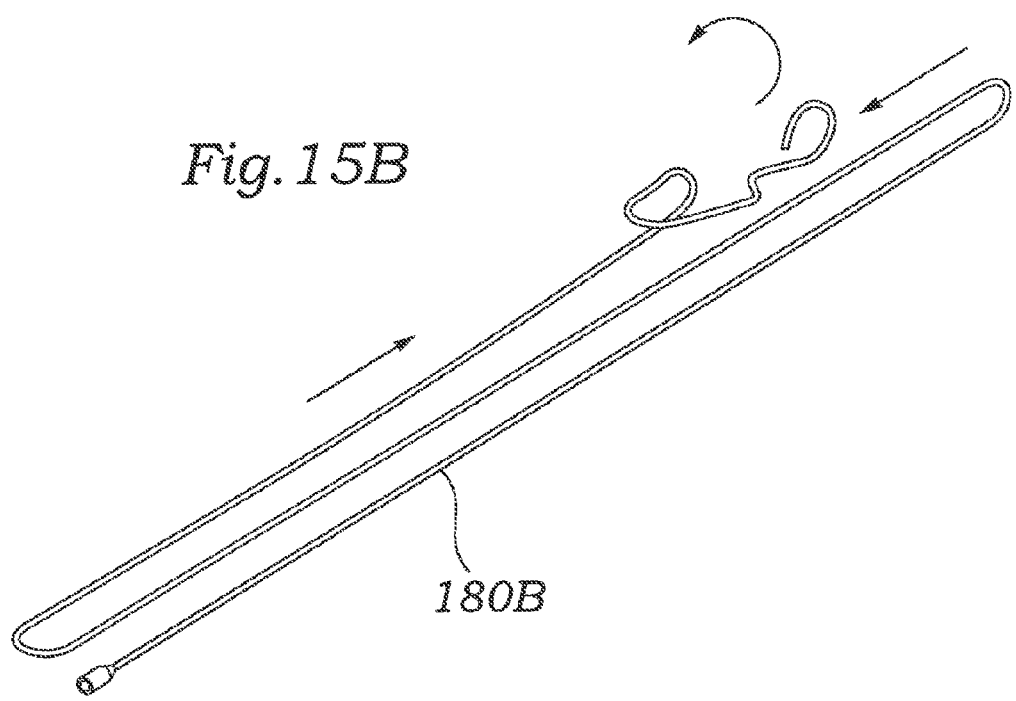

STENT DELIVERY SYSTEM

RELATED APPLICATIONS

This application is a continuation of U.S. patent application Ser. No. 11/652,737, filed Jan. 12, 2007, now U.S. Pat. No. 8,808,346, which claims priority under 35 U.S.C. §119(e) to U.S. Provisional Application No. 60/759,136, filed Jan. 13, 2006 and to U.S. Provisional Application No. 60/789,734, filed Apr. 5, 2006, each of which is incorporated by reference in its entirety into this application.

FIELD OF THE INVENTION

This invention relates broadly to medical devices. More particularly, this invention relates to an instrument for delivering a self-expanding stent into a mammalian body and controllably releasing the stent.

BACKGROUND OF THE INVENTION

Transluminal prostheses are widely used in the medical arts for implantation in blood vessels, biliary ducts, or other similar organs of the living body. These prostheses are commonly known as stents and are used to maintain, open, or dilate tubular anatomical structures.

The underlying structure of the stent can be virtually any stent design. There are typically two types of stents: self-expanding stents and balloon expandable stents. Stents are typically formed from malleable metals, such as 300 series stainless steel, or from resilient metals, such as super-elastic and shape memory alloys, e.g., Nitinol™ alloys, spring stainless steels, and the like. They can also, however, be formed from non-metal materials such as non-degradable or biodegradable polymers or from bioresorbable materials such as levorotatory polylactic acid (L-PLA), polyglycolic acid (PGA) or other materials such as those described in U.S. Pat. No. 6,660,827, the contents of which are hereby incorporated by reference.

Self-expanding stents are delivered through the body lumen on a catheter to the treatment site where the stent is released from the catheter, allowing the stent to automatically expand and come into direct contact with the luminal wall of the vessel. Examples of a self-expanding stent suitable for purposes of this invention are disclosed in U.S. Publication No. 2002/0116044, which is incorporated herein by reference. For example, the self-expanding stent described in U.S. Publication No. 2002/0116044 comprises a lattice having two different types of helices forming a hollow tube having no free ends. The first type of helix is formed from a plurality of undulations, and the second type of helix is formed from a plurality of connection elements in series with the undulations, wherein the connection elements connect fewer than all of the undulations in adjacent turns of the first type of helix. The first and second types of helices proceed circumferentially in opposite directions along the longitudinal axis of the hollow tube. This design provides a stent having a high degree of flexibility as well as radial strength. It will be apparent to those skilled in the art that other self-expanding stent designs (such as resilient metal stent designs) could be used according to this invention.

The stent may also be a balloon expandable stent which is expanded using an inflatable balloon catheter. Balloon expandable stents may be implanted by mounting the stent in an unexpanded or crimped state on a balloon segment of a catheter. The catheter, after having the crimped stent placed thereon, is inserted through a puncture in a vessel wall and moved through the vessel until it is positioned in the portion of the vessel that is in need of repair. The stent is then expanded by inflating the balloon catheter against the inside wall of the vessel. Specifically, the stent is plastically deformed by inflating the balloon so that the diameter of the stent is increased and remains at an increased state, as described in U.S. Pat. No. 6,500,248, which is incorporated herein by reference.

Stents are delivered to an implant site with the use of a delivery system. Delivery systems for self-expanding stents generally comprise an inner tubular member on which the stent is loaded and which may be fed over a guidewire, and an outer tubular member or jacket longitudinally slidable over the inner tubular member and adapted to extend over the stent during delivery to the implant site. The jacket is retracted along the inner tubular member to release the self-expanding stent from the inner tubular member.

In several available delivery systems, the jacket and inner member are freely movable relative to each other and must be separately manually held in the hands of the physician. After the distal end of the system is located at the implant site, the inner member must be held still to prevent dislocation. However, it is very difficult to maintain the position of the inner member while moving the outer member to deploy the stent. As such, the degree of control during deployment is limited. Under such limited control there is a tendency for the stent to escape from the inner member before the jacket is fully retracted and jump from the desired deployment site. This may result in deployment of the stent at a location other than the desired implant site.

A handle may be provided to move the outer tubular member relative to the inner tubular member with greater control. For example, Medtronic Inc., utilizes a handle which can lock the inner tube and outer jacket relative to each other and effect relative movement of the two to cause deployment of the stent. However, such handles have several shortcomings. First, the handle is not particularly well suited to short stents as there is little fine control. Second, the handle is not well-suited to long stents, e.g., above 90 mm in length, as the linear control requires the operator to change his or her grip during deployment in order to generate the large relative motion of the tubular components. Third, it is possible for the stent to automatically release before the jacket is fully retracted from over the stent. This is because the super-elastic expansion of the stent causes the stent to slip distally out of the deployment system before the operator retracts the sheath. The result can be an unintentionally rapid and possibly uneven deployment of the stent. Fourth, without reference to a fluoroscope monitoring the stent, there is no manner to determine from the proximal end of the instrument the progress of stent deployment. Fifth, the construction of the inner tubular member and outer jacket may cause the inner member and jacket to be crushed during use. Furthermore, the inner tubular member is subject to compressive force during deployment and may deform while moving the stent from the desired deployment location.

Another stent delivery system can be seen in the U.S. Publication No. 2004/0006380 titled Stent Delivery System and U.S. Publication No. 2005/0273151 also titled Stent Delivery System, the contents of which are hereby incorporated by reference. Like other available stent delivery systems, the designs in these publications provide a single actuating mechanism for moving the outer jacket relative to the inner tubular member, specifically shown as a thumbwheel.

In these designs, the retraction speed of the jacket member is limited by both the user's ability to actuate the thumbwheel (i.e. the speed the user can move their thumb) and the retraction ratio of the thumbwheel (i.e. the ratio of thumbwheel movement/rotation to jacket retraction). This "speed limit" can be especially difficult for a user when deploying longer stents such as those between 100 and 200 mm in length, since it greatly increases the stent deployment time. Further, the thumbwheel can have only one retraction ratio, which increases the difficulty of retracting the jacket at substantially different speeds.

What is needed is a stent delivery system that overcomes the limitations of the prior art and facilitates the retraction of the jacket at different speeds. Further, a stent delivery system is needed that provides the user with greater dynamic control of the jacket to increase delivery precision while reducing the deployment time.

OBJECTS AND SUMMARY OF THE INVENTION

It is therefore an object of the invention to provide a stent delivery system that permits a high degree of control during the deployment of the stent.

It is another object of the invention to provide a stent delivery system that more easily retracts an outer jacket at different speeds.

It is another object of the invention to provide a stent delivery system that has multiple controls for retracting an outer jacket.

It is yet another object of the invention to provide a stent delivery system with independent outer jacket retraction controls that allow switching from one control to another without a lag in the jacket retraction.

The present invention seeks to achieve these and other objects in one preferred embodiment by providing a stent delivery system having three independent controls for retracting an outer jacket to deliver a stent or similar prosthesis. More specifically, the stent delivery system provides a thumbwheel, a thumb lever, and a pull ring which each engage a distal portion of the outer jacket. When any of the three controls are actuated, they create a proximal force on the jacket, retracting the jacket and releasing a stent on the distal end of the delivery system.

Preferably, the thumbwheel and the thumb lever retract the jacket by way of a cord within the handle of the delivery system that engages a proximal portion of the jacket. The thumbwheel rotates a spool which winds up the cord and therefore causes the jacket to retract. The thumb lever effectively increases the path of the cord within the handle by moving against a region of the cord, also causing the jacket to retract. The pull ring is preferably connected to the proximal end of the jacket, allowing the user to directly pull the jacket in a proximal direction.

Each of the jacket controls can be configured to provide the user with different retraction ratios (e.g. for every 1 cm of movement of the thumb lever the jacket retracts 2 cm). In this respect, the user can use different retraction controls at different stages in the delivery procedure. For example, the user may wish to initially retract the jacket slowly to "flower" the stent, with the thumbwheel. However, once the stent has been flowered, the user may wish to more quickly retract the jacket with the lower ratio of the thumb lever or pull ring. In this respect, the stent delivery system allows the user to more easily retract the jacket at different speeds during the delivery procedure.

Additional objects and advantages of the invention will become apparent to those skilled in the art upon reference to the detailed description taken in conjunction with the provided figures.

BRIEF DESCRIPTION OF THE DRAWINGS

FIG. 11 illustrates a perspective view of a slider of a handle portion of FIG. 1;

FIG. 12 illustrates a perspective view of a slider of the delivery system of FIG. 1;

FIG. 13 illustrates a side view of the slider of FIG. 12;

FIGS. 15A-15D illustrate perspective views of cord paths according to a preferred embodiment of the present invention;

DETAILED DESCRIPTION OF THE INVENTION

Figure 1:
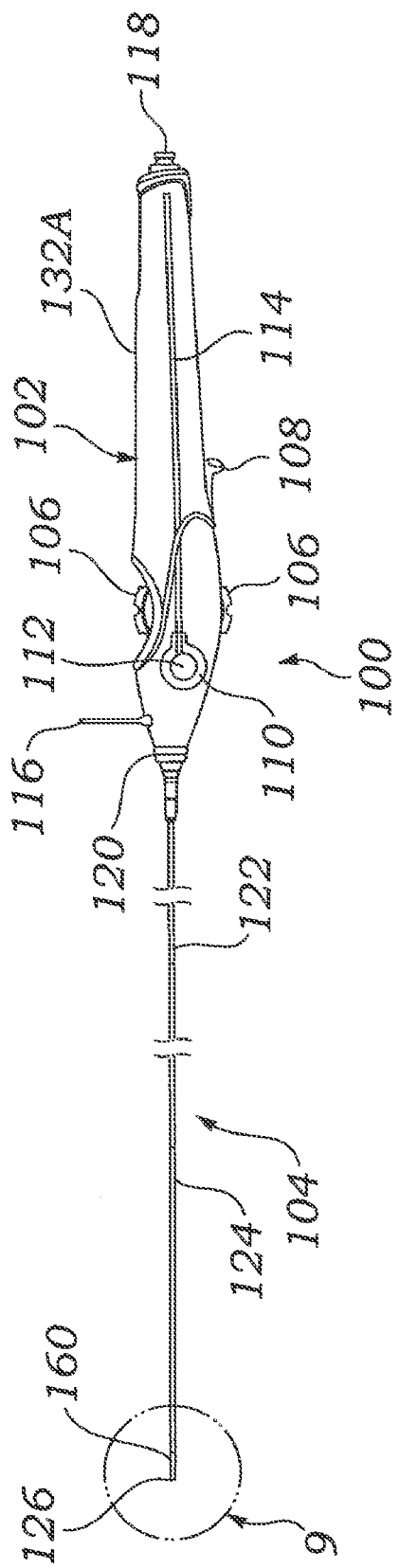
FIG. 1 illustrates a side view of a preferred embodiment of a delivery system according to the present invention.

FIGS. 1-14 illustrate a preferred embodiment of a stent delivery system 100 according to the present invention which includes multiple mechanisms for retracting an outer tubular member 124 (also referred to as a jacket or sheath in this specification) to deliver a prosthesis, such as a stent 160 in the current example. As seen in FIG. 1, the stent delivery system 100 includes a thumbwheel 106, a deployment lever 108, and a rapid deployment ring 110, each providing a different approach to retracting the outer tubular member 124 and therefore deploying the stent 160 or other prosthesis.

Each of the three deployment controls provides different actuation methods that facilitate deployment of the stent 160 at different speeds. For example, the thumbwheel 106 allows the user to slowly deploy the stent 160 with slow and precise thumb movement, while the rapid deployment ring 110 provides the user leverage to deploy the stent 160 in a more rapid fashion.

Additionally, some of the deployment controls can be configured to provide different ratios of retraction (e.g. 1 cm of movement of the deployment lever 108 moves the outer tubular member 124, 2 cm). Thus, some controls may provide "finer" retraction control (i.e. smaller movement of the outer tubular member 124) and other controls may provide a "coarser" retraction control (i.e. larger movement of the outer tubular member 124).

In this respect, the delivery system 100 provides the user with a wider, more dynamic range of deployment controls for more precisely delivering the stent 160 within a patient. Further, this range of deployment controls can better accommodate different types of stents or prostheses, especially those of almost any length.

The stent delivery system 100 generally includes two main portions: a stent delivery portion 104 and a handle portion 102. The stent delivery portion 104 is the elongated catheter assembly which is inserted into the patient to deliver the stent 160 at a desired location. The handle portion 102 is connected to a proximal end of the stent delivery portion 104, allowing the user to position the stent delivery portion 104 within the patient and release the stent 160.

As best seen in FIGS. 1 and 6-8, the stent delivery portion 104 includes an inner tubular member 128 preferably composed of a relatively stiff single material (e.g. polyimide) that preferably forms a single inner lumen. This allows the inner tubular member 128 to maintain some flexibility while retaining the strength to be pushed through the inner vessels of a patient.

Figure 7:
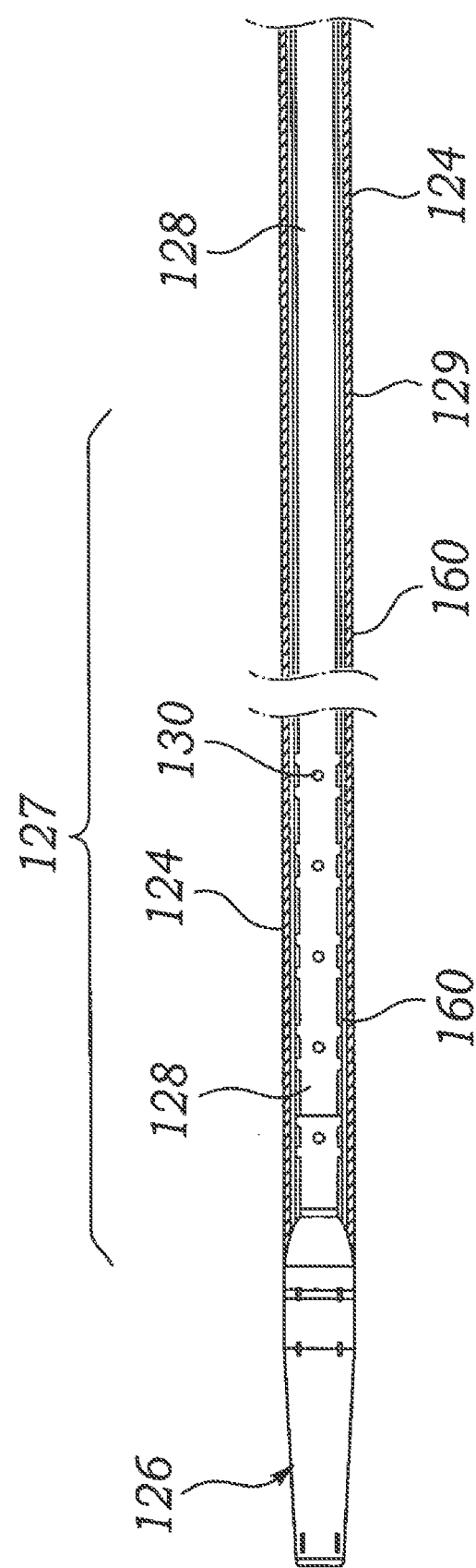
FIG. 7 illustrates a side cross section view of a distal end of the delivery portion of the delivery system of FIG. 1.

With reference to FIG. 7, the distal end of the inner tubular member 128 includes a reduced diameter region 127 between a distal dilator tip 126 (preferably composed of polyimide) and a shoulder 129. The reduced diameter region provides space to accommodate the stent 160 in an unexpanded position underneath the outer tubular member 124. The shoulder 129 and the distal dilator tip 126 prevent the stent from moving laterally on the inner tubular member 128, either proximally toward the handle portion 102 or distally out from under the outer tubular member 124. The delivery portion may also include pusher tubing that is disposed over the inner tubular member 128, proximal to a shoulder 129, which further supports the stent 160 when the outer tubular member 124 retracts during delivery. In this respect, the stent 160 maintains its position within the stent delivery system 100, providing a predictable delivery for the user.

As also seen in FIG. 7, the distal end of the inner tubular member 128 also includes flushing holes 130, which are positioned underneath the stent 160 in the reduced diameter region 127 and which lead to, and are unitary with, a passage (not shown) within the inner tubular member 128, along its axis. This inner passage or lumen connects to a liquid source on the proximal end of the stent delivery system 100 at luer adapter 118, allowing the user to flush out the stent 160 prior to delivery within the patient.

Figure 6:
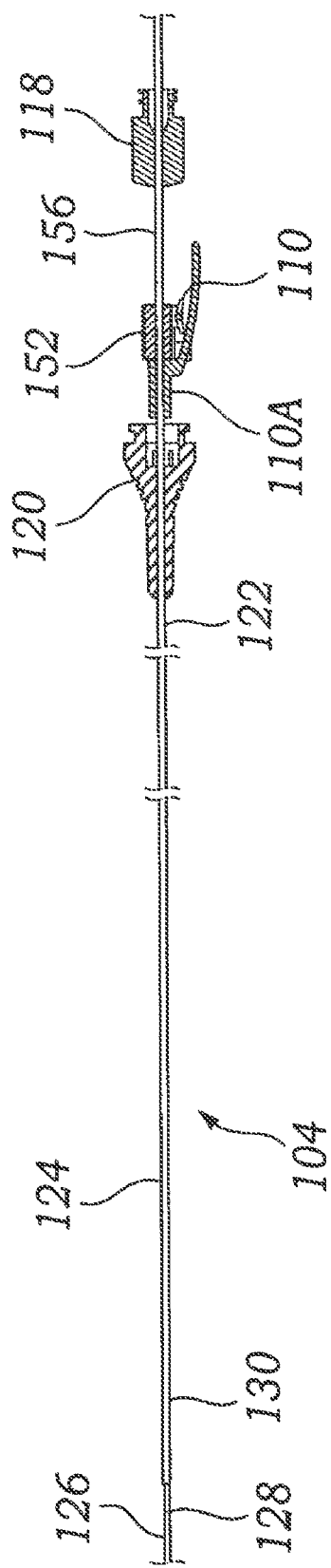
FIG. 6 illustrates a side cross section view of a delivery portion of the delivery system of FIG. 1.

As best seen in FIG. 6, the proximal end of the inner tubular member 128 comprises a rigid area 156 composed of less flexible materials, such as metals or hard plastics. This rigid area 156 is positioned within the handle portion 102, allowing the outer tubular member 124 to be easily retracted over the rigid area 156 without the inner tubular member 128 bending or creasing. The movement of the outer tubular member 124 over the inner tubular member 128 is discussed in greater detail below.

As previously mentioned, the outer tubular member 124 is positioned over the inner tubular member 128 and can be moved relative to the inner tubular member 128, particularly allowing the outer tubular member 124 to cover and uncover the nnexpanded stent 160. Preferably, the outer tubular member 124 is composed of a braided polyimide. Alternately, the outer tubular member 124 is composed of a coextruded, trilayer construction. The inner layer is preferably polytetrafluoroethylene (PTFE), fluorinated ethylene propylene (FEP), high density polyethylene (HDPE), or urethane. The middle layer is a wire braid, and more preferably a 304V stainless steel flat wire braid of 1×3 (40 picks) construction, with wires having a 0.001 inch by 0.003 inch rectangular cross-section. Wires of other metals and alloys may also be used, including other stainless steel alloys, cobalt-chrome alloys, and other high-strength, high-stiffness, corrosion-resistant metal alloys. The outer layer is preferably a thermoplastic, melt processible, polyether-based polyamide, such as PEBAX®-7033 available from Modified Polymer Components, Inc. of Sunnyvale, Calif. In the extrusion process, the inner and outer layers are bonded to each other and encapsulate the metallic reinforcing middle wire layer to create an integrated tubing. This tubing exhibits high lateral flexibility combined with a high degree of longitudinal stiffness (resistance to shortening), and also high torqueability.

Figure 8:
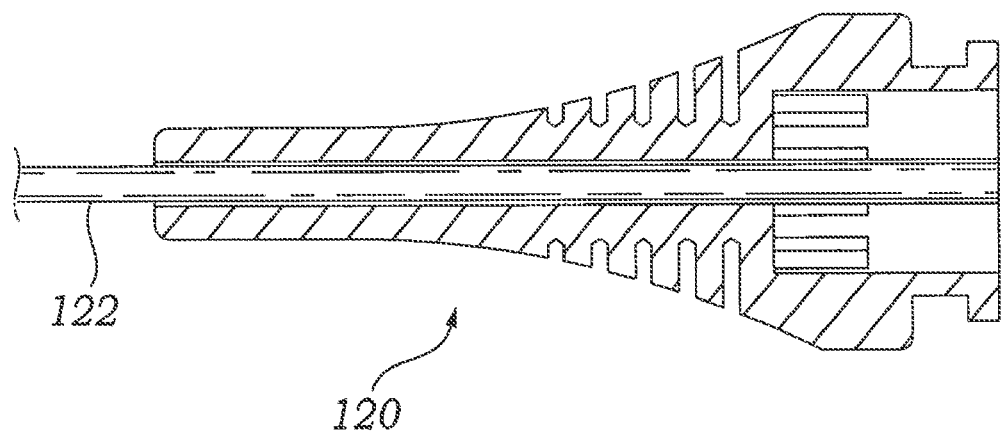
FIG. 8 illustrates a side cross section view of a strain relief member of the delivery system of FIG. 1.

Referring to FIGS. 1, 6 and 8, stability sheath 122 and strain relief member 120 are connected to the handle portion 102 and are positioned over the outer tubular member 124. The strain relief member 120 (preferably composed of Polyurethane or Pebax® polyether block amides from Arkema) prevents sharp bends in the outer tubular member 124 near the handle portion 102, reducing stress or strain that may otherwise be introduced on connection points between the handle portion 102 and the outer tubular member 124. The stability sheath 122 extends along a portion of the length of the outer tubular member 124 to reduce any unintended movement of the stent delivery portion 104 while the outer tubular member 124 is being retracted (e.g. sideways or curling movement due to friction between the outer tubular member 124 and the inner tubular member 128).

As best seen in FIGS. 1-5, the handle portion 102 preferably includes three mechanisms for retracting the outer tubular member 124 relative to the inner tubular member 128. Specifically, the handle portion 102 includes the thumbwheel 106, the deployment lever 108, and the rapid deployment ring 110 that each are used to cause retraction of the outer tubular member 124 through different mechanisms within the handle portion 102.

Figure 2:
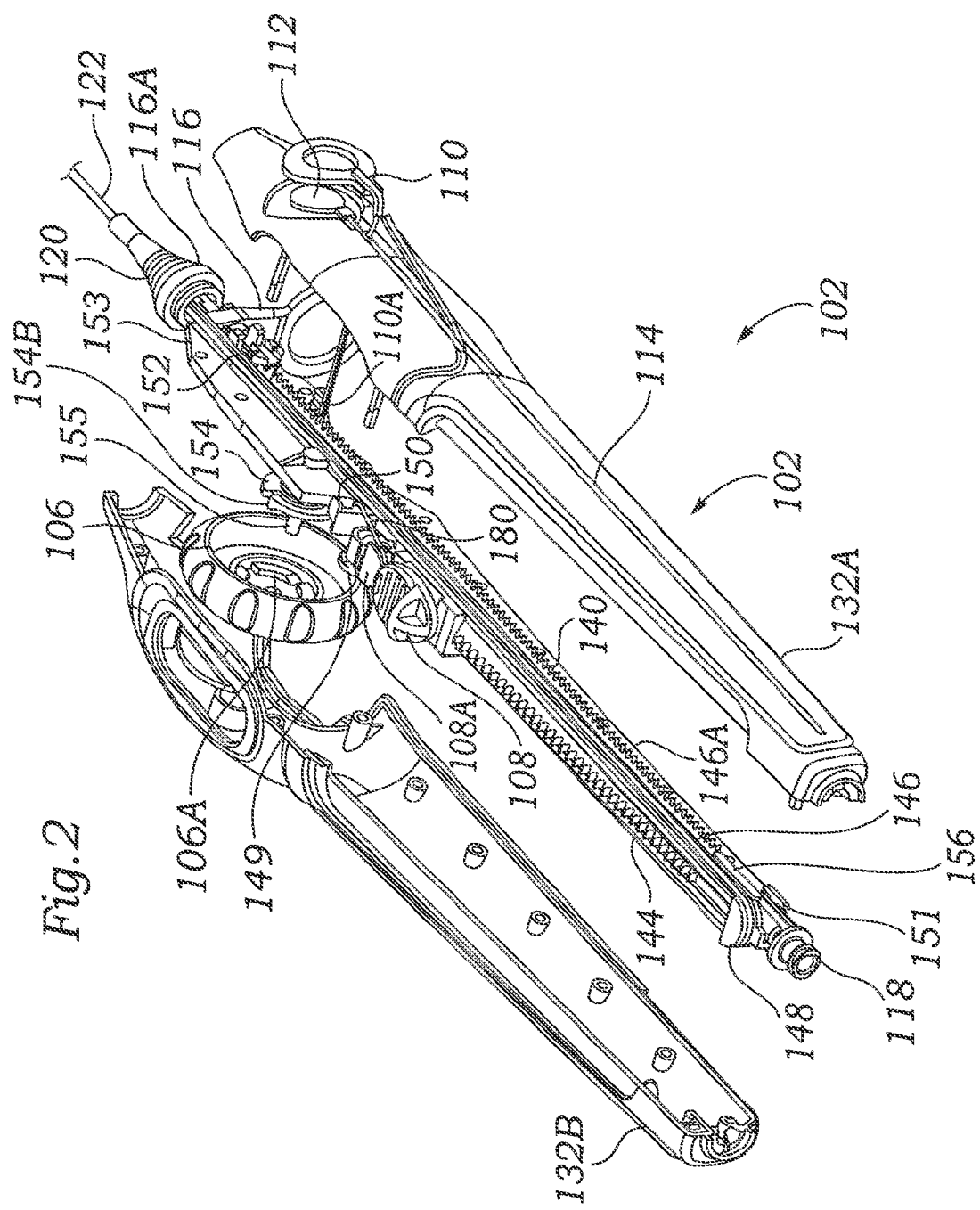
FIG. 2 illustrates an exploded perspective view of the delivery system of FIG. 1.
Figure 3:
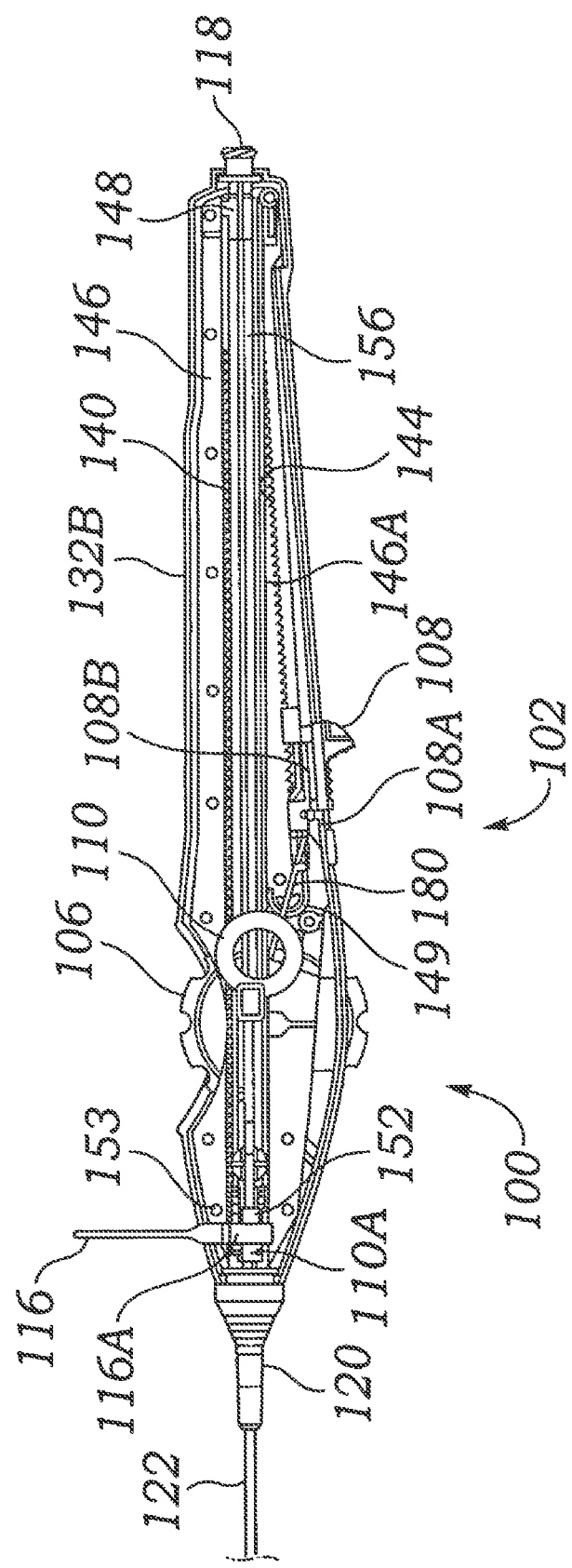
FIG. 3 illustrates a partially disassembled side view of the delivery system of FIG. 1.
Figure 4:
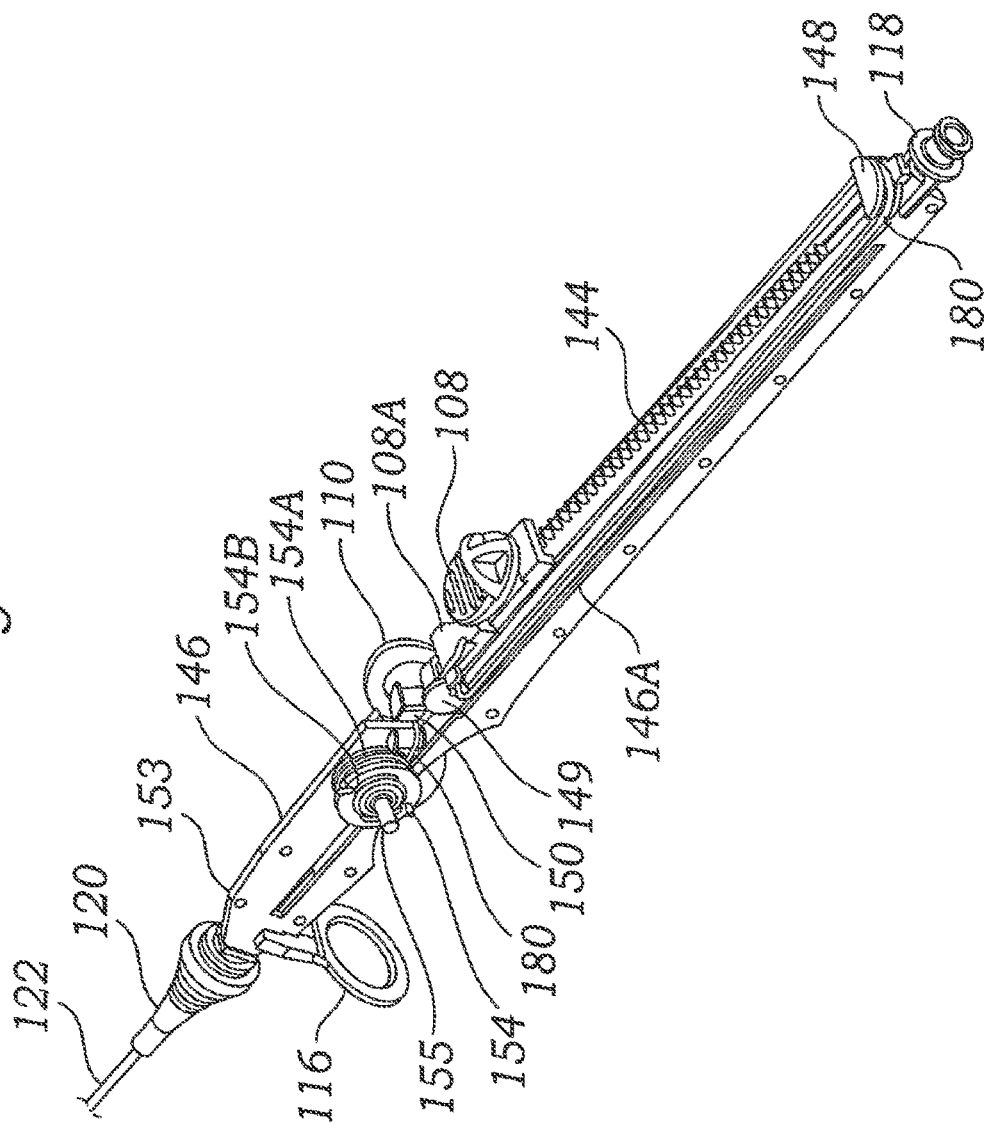
FIG. 4 illustrates a partially disassembled perspective view of the delivery system of FIG. 1.
Figure 5:
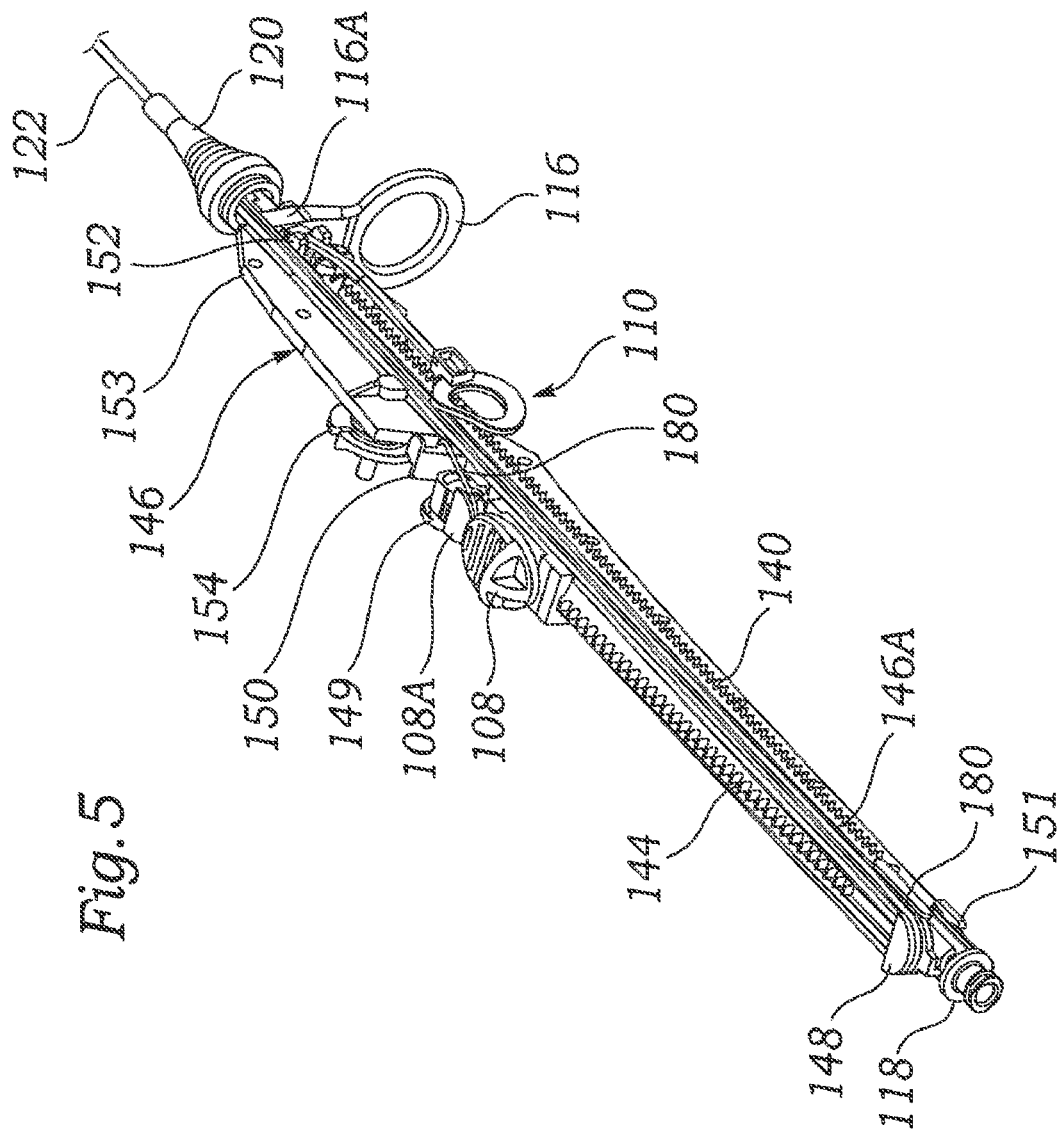
FIG. 5 illustrates a partially disassembled perspective view of the delivery system of FIG. 1.

Referring to FIG. 2-5 the retraction mechanisms are built on an inner frame member 146 that is enclosed by body shell members 132A and 132B. As seen in FIGS. 2 and 11 the inner frame member 146 includes an elongated slot 146A that extends most of the length of the frame member 146. A slider 152, best seen in FIG. 11-13, is positioned through and engaged with the slot 146A so as to slide along the length of the slot 146A. The slider 152 is also fixed to the proximal end of the outer tubular member 124, preferably by an adhesive. Thus, as the slider 152 slides from a distal end of the slot 146A to a proximal end of the slot 146A, the outer tubular member 124 similarly moves over the rigid area 156 of the inner tubular member 128.

Optionally, a portion of the slider 152 contacts rack 140 to provide a tactile and audible "click" as the slider 152 slides proximally along the slot 146A. The teeth of the rack 140 also allow the slider 152 to move in only a proximal direction by including an angled distal surface and a perpendicular proximal surface. Thus, the contacting portion of the slider 152 simply moves up and over the angled surface when moved proximally, but is stopped from movement by the perpendicular surface when distal movement is attempted. These "one way" teeth prevent the user from moving the outer tubular member 124 distally in an attempt to recapture a partially deployed stent 160.

The thumbwheel 106, deployment lever 108, and the rapid deployment ring 110 can each apply force in a proximal direction to the slider 152, causing the slider 152 and therefore the outer tubular member 124 to move in a proximal direction. As described in more detail below, each deployment control uses different mechanisms within the handle portion 102 to create force on the slider 152. The distance the slider 152 moves will vary between each deployment control based, at least in part, on how the mechanisms of each deployment control are configured. These mechanisms and their possible configurations will become clear from the description below.

As seen best in FIGS. 2, 4, 9 and 10, the thumbwheel 106 provides proximal force on the slider 152 through use of a cord 180 wound on a spool 154 at one end and attached to the slider 152 at the other end. The cord 180 is either attached to or positioned around the slider 152 so that increased tension on the cord 180 provides a proximal force on the slider 152, ultimately causing movement of the both the slider 152 and the outer tubular member 124.

Preferably the cord 180 is composed of a material that imparts little or no stretch to the length of the cord 180. For example, polyethylene, nylon, stainless steel wire, or braided stainless steel fibers. While a cord 180 is preferred in the present preferred embodiment, almost any flexible elongated member could be used, having different shapes, thicknesses, flexibilities and compositions. For example, a relatively flat ribbon shape may be used or alternately a cord having a generally square cross section. In another example, the cord can be composed of a single, continuous material such as all plastic, or multiple threads woven together.

Turning first to the rotation of the spool 154, a side of the inner frame member 146 includes an axle 155 onto which the spool 154 and the thumbwheel 106 rotatably mount by way of apertures through their respective centers. When the handle portion 102 is fully assembled, the spool 154 is positioned within the thumbwheel 106, pressing against a side of thumbwheel 106.

Figure 9:
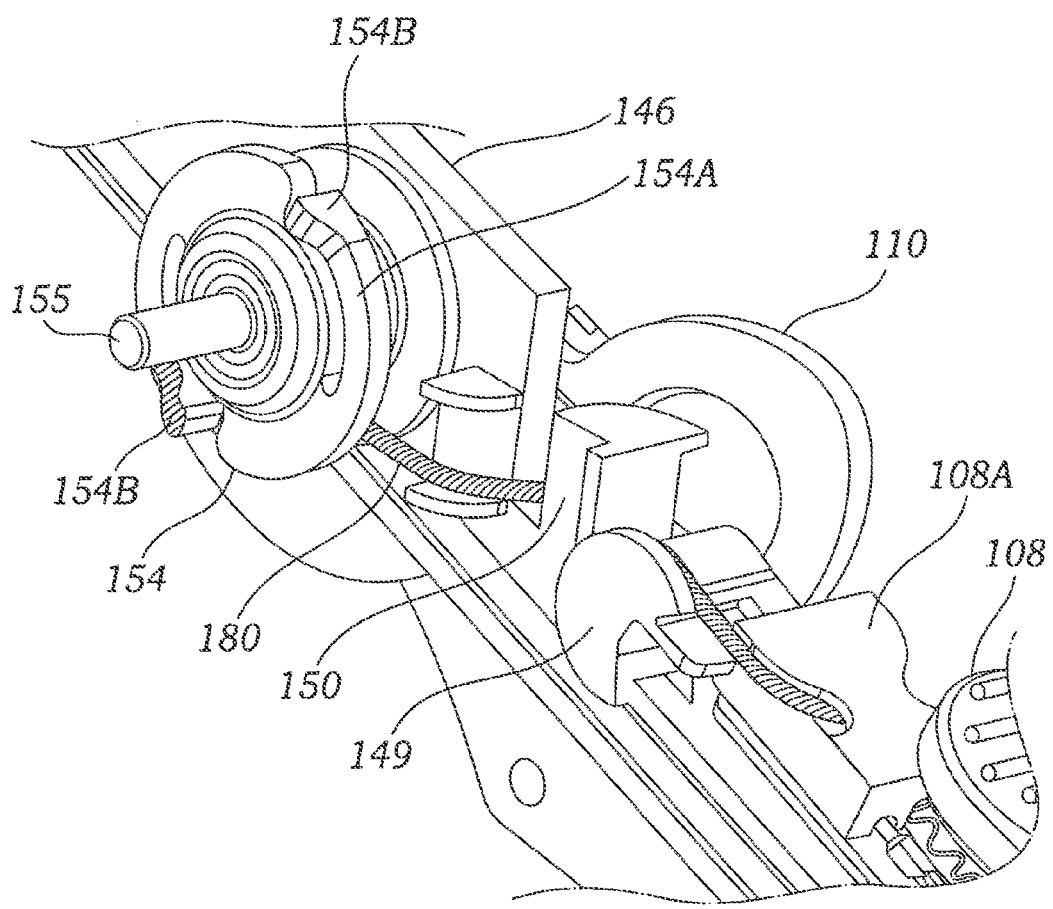
FIG. 9 illustrates a perspective view of a spool of the delivery system of FIG. 1.
Figure 10:
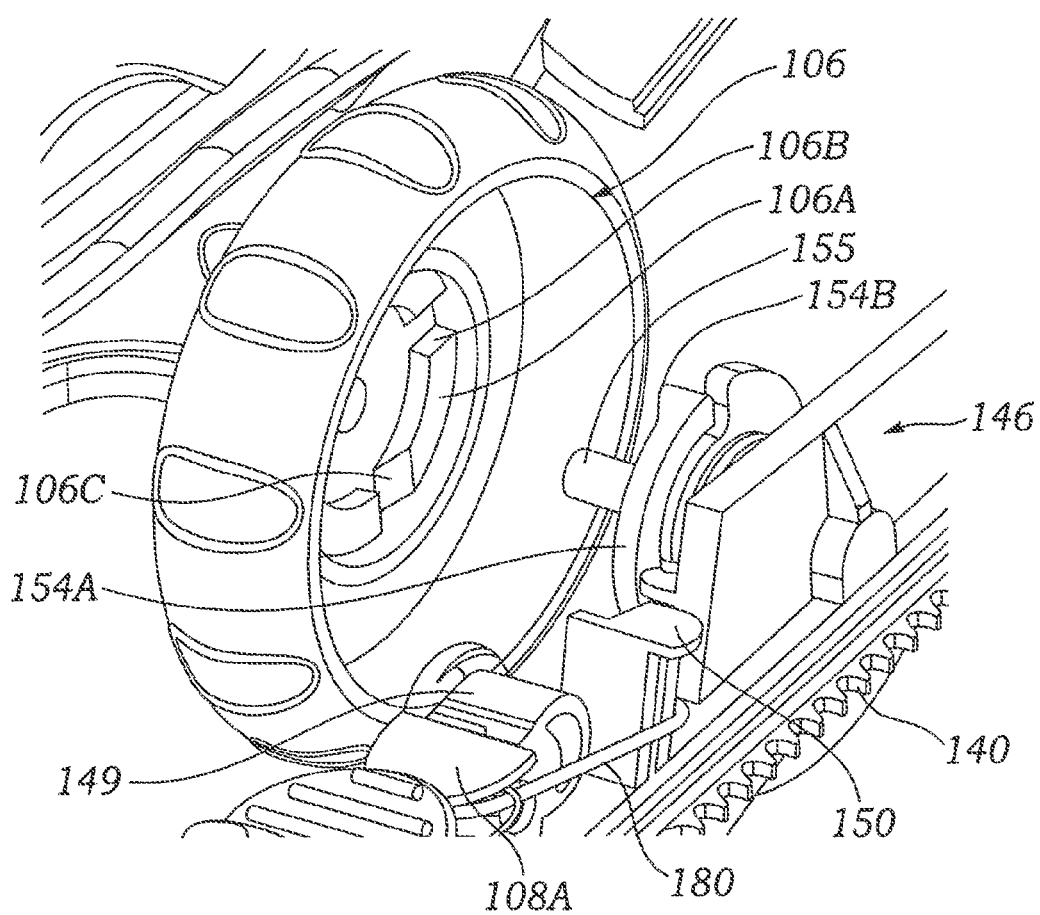
FIG. 10 illustrates a perspective view of a thumbwheel of the delivery system of FIG. 1.

As best seen in FIGS. 9 and 10, the thumbwheel 106 engages the spool 154 with a "one way" engagement mechanism that allows the thumbwheel 106 to only engage and rotate the spool 154 in one direction. In this respect, the user is limited to retracting the outer tubular member 124 only, preventing attempts to recapture a partially deployed stent 160.

The engagement mechanism includes raised members 106A, seen best in FIG. 10, positioned in a circular pattern on the inner surface of the thumbwheel 106. Each raised member 106A includes a flat surface 106B perpendicular to the inner surface of the thumbwheel 106 and an angled surface 106C. The angled surface 106C of one raised member 106A is positioned near the flat surface 106B of another raised member 106A, orienting all of the surfaces in a single direction (e.g. all angled surfaces 106C face a clockwise direction while all flat surfaces 106B face a counter clockwise direction).

The spool 154 includes two floating arms 154A having an outwardly extending region 154B, positioned to have a similar circumferential position as raised members 106A. When the handle portion 102 is assembled, the extending region 154B contacts either the raised members 106A or the space in between the raised members 106A, depending on the rotational orientation of the thumbwheel 106. As the thumbwheel 106 is rotated in one direction, the flat sides 106B of the raised members 106A contact the extending region 154B, causing the spool 154 to rotate and therefore wind up the cord 180.

However, if the thumbwheel 106 is rotated in the opposite direction, the angled surface 106 contacts the extending region 154B, causing the floating arm 154A to move towards the inner frame member 146. As the thumbwheel 106 continues to rotate, the extending region 154B passes over the top of raised member 106A until the end of the raised member 106A is reached, at which time the floating arm 154A snaps back to its original position. Thus, the thumbwheel 106 rotates, but the spool 154 is not engaged and therefore does not rotate, effectively limiting rotation of the spool 154 by the thumbwheel 106 to only one direction.

As previously described, rotation of the spool 154 winds one end of the cord 180, reducing the effective length of the cord 180 in the handle portion 102. However, the cord 180 must also be appropriately positioned within the handle portion 102 to create a proximal force on the slider 152. This cord position or cord path can be more clearly observed by comparing the exploded view of FIG. 2 with the cord 180 shown in FIG. 15A. As seen in these figures, one end of the cord 180 is wrapped around the spool 154, passing around stationary anchor member 150 that is fixed to the inner frame member 146, through a passage 108A of the movable deployment lever 108, back around a stationary anchor 149 that is also fixed on the inner frame member 146, then passing down along the side of inner frame member 146, around anchor member 148 at the proximal end of the inner frame member 146 and extending back towards the distal end of the inner frame member 146, and finally terminating with a knot around slider 152. Each of the stationary anchors has curved surfaces upon which the cord 180 can easily travel. Thus, as the spool 154 rotates in one direction (depending which direction the spool 154 is configured to wind the cord 180), the cord 180 pulls the slider 152 towards the proximal end of the handle portion 102.

The mechanisms of the deployment controls, as previously mentioned, can be configured to change the retraction ratio of the outer tubular member 124. In one example, the mechanisms of the thumbwheel 106 can be modified by changing the size of the spool 154. More specifically, the size of the spool 154 (i.e. the spool diameter) can be increased or decreased to change the amount of cord 180 each rotation of the thumbwheel 106 takes up. For example, decreasing the size of the spool 154 will reduce the amount of cord 180 taken up by each rotation of the thumbwheel 106 and therefore reduces the amount the outer tubular member 124 is retracted. Similarly, increasing the size of the spool 154 will increase the amount of cord 180 taken up by each rotation of the thumbwheel 106, increasing the amount the outer tubular member 124 is retracted.

Turning to the second deployment control, the deployment lever 108, can also retract the slider 152 and therefore the outer tubular member 124 by increasing tension on the cord 180 and therefore on the slider 152 as well. As seen in FIGS. 1-5, the deployment lever 108 engages a top portion of the inner frame member 146 over a rack 144, sliding in a proximal direction along the top portion of the inner frame member 146. As the deployment lever 108 moves in a proximal direction, it increases the path the cord 180 takes to reach the slider 152, increasing the tension on the cord 180 and generating a proximal force on the slider 152.

Like the thumbwheel 106 and the slider 152, the deployment lever 108 only moves in one direction, allowing the user to only retract the outer tubular member 124. This "one way" movement is preferably achieved with a direction arm 108B (FIG. 3) extending from a proximal end of the underside of the deployment lever 108. This direction arm 108B includes an end portion that engages the teeth of a rack 144. As seen best in FIG. 3, the teeth of the rack 144 have a distal surface that is angled and a proximal surface that is generally perpendicular to the inner frame member 146. When the deployment lever 108 is moved in a proximal direction, the direction arm 108B follows the angled distal surface upward, moving over and past each tooth. However, when the deployment lever 108 is moved in a distal direction, the end of direction arm 108B moves against the perpendicular proximal surface of the tooth. Since the proximal surface is not angled beyond 90 degrees (i.e. beyond the perpendicular) the direction arm 108B is unable to move over the tooth. Thus, the direction arm 108B prevents the deployment lever 108 from moving in a distal direction, to recapture the stent 160. Additionally, the position of the deployment lever 108 is maintained when the user rotates the thumbwheel 106, which may create a distal force on the lever 108 as the tension on the cord 180 is increased.

Referring to FIGS. 2-5, the proximal movement of the deployment lever 108 moves the slider 152 by effectively increasing the length of the path that the cord 180 must take to reach the slider 152. As previously mentioned, the cord 180 passes through the passage 108A of the movable deployment lever 108, around the stationary anchor member 149 that is fixed on the inner frame member 146, down the length of the inner frame member 146, then around stationary anchor member 148 at the proximal end of inner frame member 146. As the deployment lever 108 is moved in a proximal direction, the passage 108A on the deployment lever 108 moves away from the anchor member 149 that is fixed on the inner frame member 146. As a result, the distance between the passage 108A and the anchor member 149 increases, creating a longer path for the cord 180. Since one end of the cord 180 is fixed around the spool 154, the movement of the deployment lever 108 in this manner causes the slider 152 and therefore the outer tubular member 124 to move proximally. In this respect, the one-way, proximal movement of the deployment lever 108 can retract the outer tubular member 124 to deploy the stent 160 within the patient.

The rapid deployment ring 110 provides yet another method of retracting the outer tubular member 124 within the handle portion 102. As seen best in FIGS. 2-6, 11 and 13, the rapid deployment ring 110 is a pull tab having an elongated body and a sliding portion 110A shaped to slidably couple to the outer tubular member 124, distal to the slider 152. The sliding portion 110A preferably has an aperture that allows it to not only be positioned onto the diameter of the outer tubular member 124, but also freely slide along its length.

As shown in FIGS. 11 and 13, when the rapid deployment ring 110 is pulled by the user in a proximal direction, the sliding portion 110A pushes on a distal side of the slider 152 in a proximal direction also, moving the slider 152 proximally and causing the outer tubular member 124 to retract. Since the rapid deployment ring 110 via its sliding portion 110A applies direct force on the slider 152 without any intervening mechanisms (i.e. in a 1:1 retraction ratio), the user is free to retract the outer tubular member 124 at any speed they desire. This arrangement especially facilitates quick retraction of the outer tubular member 124 that would otherwise be difficult using the thumbwheel 106 or deployment lever 108.

Referring to FIGS. 1 and 2, the ring portion of the rapid deployment ring 110 is positioned through a slot 114 in shell member 132A and stores on a raised column 112. The raised column 112 has a diameter about the same size as the diameter of the aperture of the rapid deployment ring 110, allowing the ring 110 to lock on to the raised column 112. Optionally, the raised column 112 may also include an "imprint" or depression around the raised column 112 which is the size and shape of the ring portion of the rapid deployment ring 110 and which allows the ring portion to sit within the depression without falling out. Thus, the rapid deployment ring 110 can be kept out of the way if the user decides to deploy the stent 160 with the thumbwheel 106 or deployment lever 108. Further, since the sliding portion 110A can freely slide along the outer tubular member 124 (i.e. is not fixed or adhered in place on the member 124), use of the thumbwheel 106 or deployment lever 108 will not cause the rapid deployment ring 110 to come loose from the raised column 112 and move down the slot 144. In other words, the position of the rapid deployment ring 110 is not affected when other deployment controls are actuated by the user.

Preferably, as seen in FIGS. 11-13, the sliding portion 110A has a thin, side profile to allow a finger member 116A of a locking clip 116 to be positioned over both the sliding portion 110A and the slider 152. Since the slider 152 has horizontally raised portions around both a proximal and a distal side of the finger 116A of the locking clip 116, the slider 152 moves against this finger 116A and is prevented from lateral movement. In this respect, the finger 116A of the locking clip 116 acts as a locking pin that prevents the stent 160 from accidentally being deployed during shipment or prior to insertion within a patient.

The retraction ratio for both the deployment lever 108 and the thumbwheel 106 can be further adjusted by changing the path of the cord 180 within the handle portion 102. One preferred method of changing this ratio is to distribute the user's retraction force over an increased the number anchors (e.g. anchor members 148 or 149). In this respect, the anchor members and cord 180 act similar to a rope and pulley system where additional anchors function as additional pulleys. Like a pulley system, the more anchors the cord 180 is positioned around, the less the outer tubular member 124 will move relative to either the thumbwheel 106 or deployment lever 108 (and the easier it will be to move the thumbwheel 106 or deployment lever 108).

Figure 14:
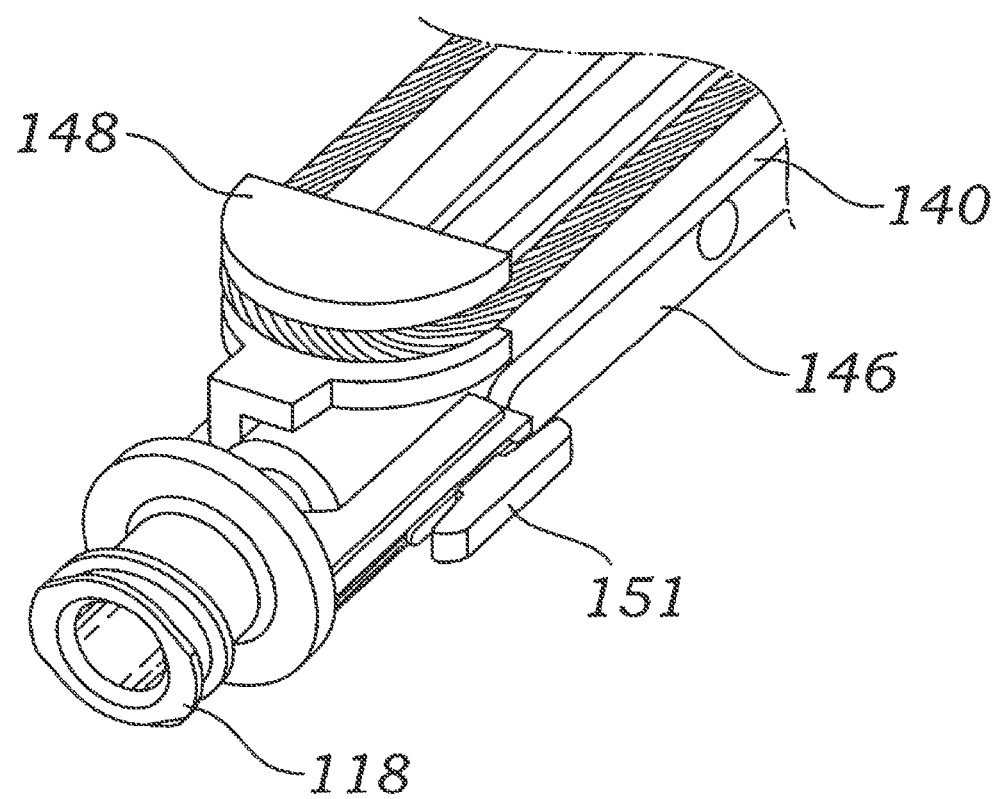
FIG. 14 illustrates a perspective view of proximal end of the delivery system of FIG. 1.
Figure 15A:
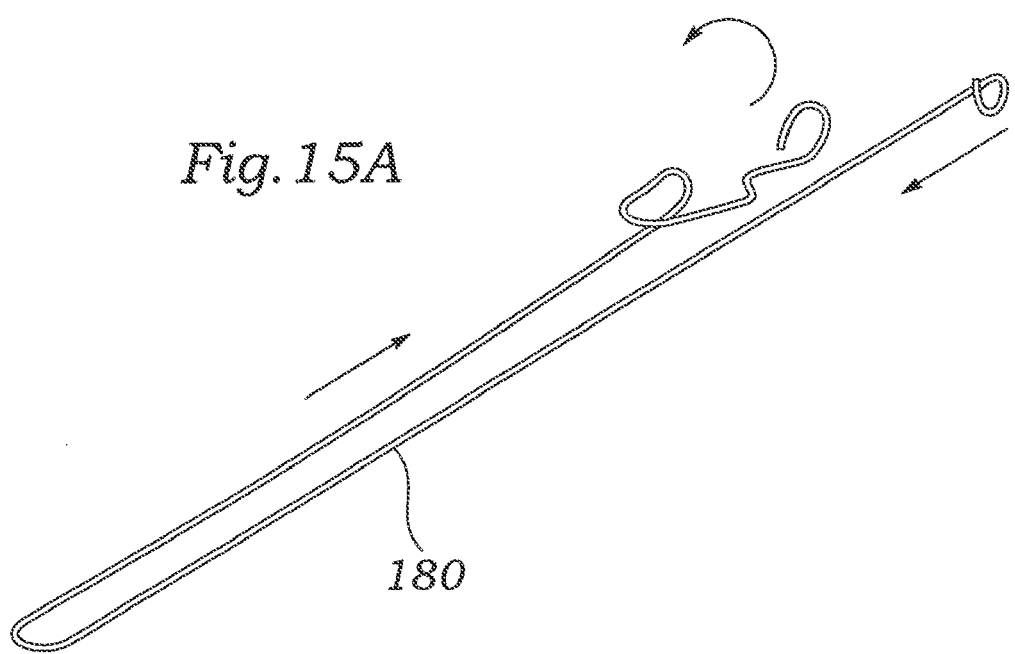

A more specific example of this concept can be seen in FIG. 15B in which the cord 180B is positioned in a configuration generally similar to that of FIG. 15A. However, instead of terminating the cord 180B at the slider 152, as seen in FIGS. 2-5, the cord 180 passes around the slider 152 and terminates at a rear anchor 151, as shown in FIG. 14 at the proximal end of inner frame member 146. In this respect, the thumbwheel 106 or deployment lever 108 moves the outer tubular member 124 a smaller amount relative to the configuration shown in FIG. 15A because of the pulley effect previously described.

Figure 15C:
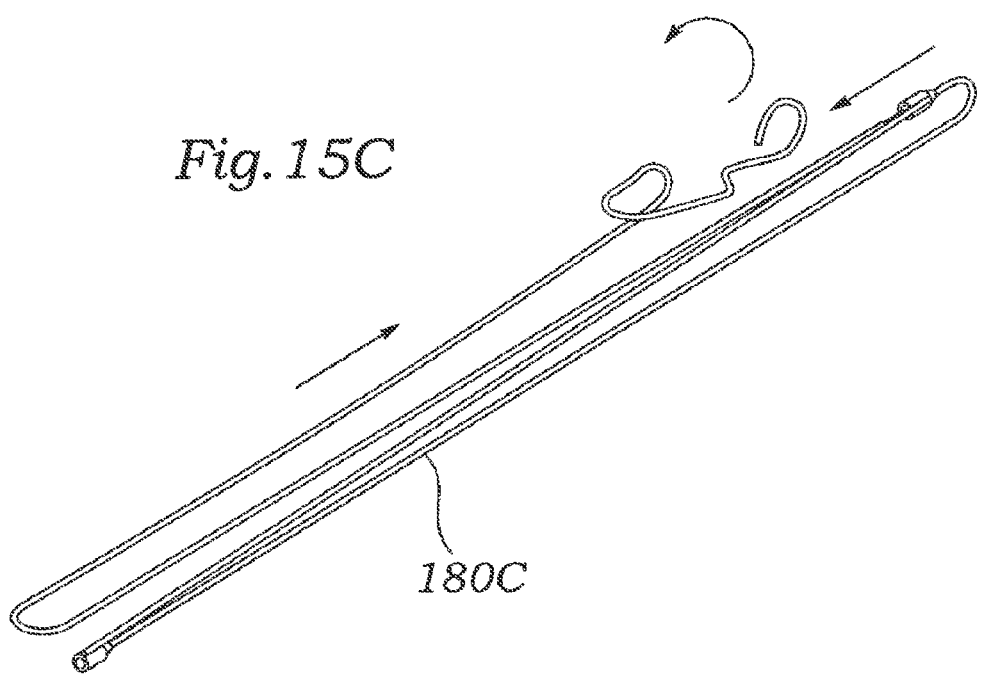

Yet another specific example can be seen in FIG. 15C, which can be compared with the structures seen in FIGS. 2-5. In this example, one end of cord 180C is wrapped around the spool 154 as previously described, passing around a stationary anchor member 150 located on a top region of inner frame member 146, through passage 108A of the movable deployment lever 108, back around anchor member 148, forward around slider 152, back around anchor member 151, and finally tying through aperture 153 which is located on a distal portion of the inner frame member 146. Similarly, the thumbwheel 106 or deployment lever 108 move the outer tubular member 124 a smaller amount relative to the configurations shown in FIGS. 15A and 15B due to the previously described pulley effect.

Figure 15D:
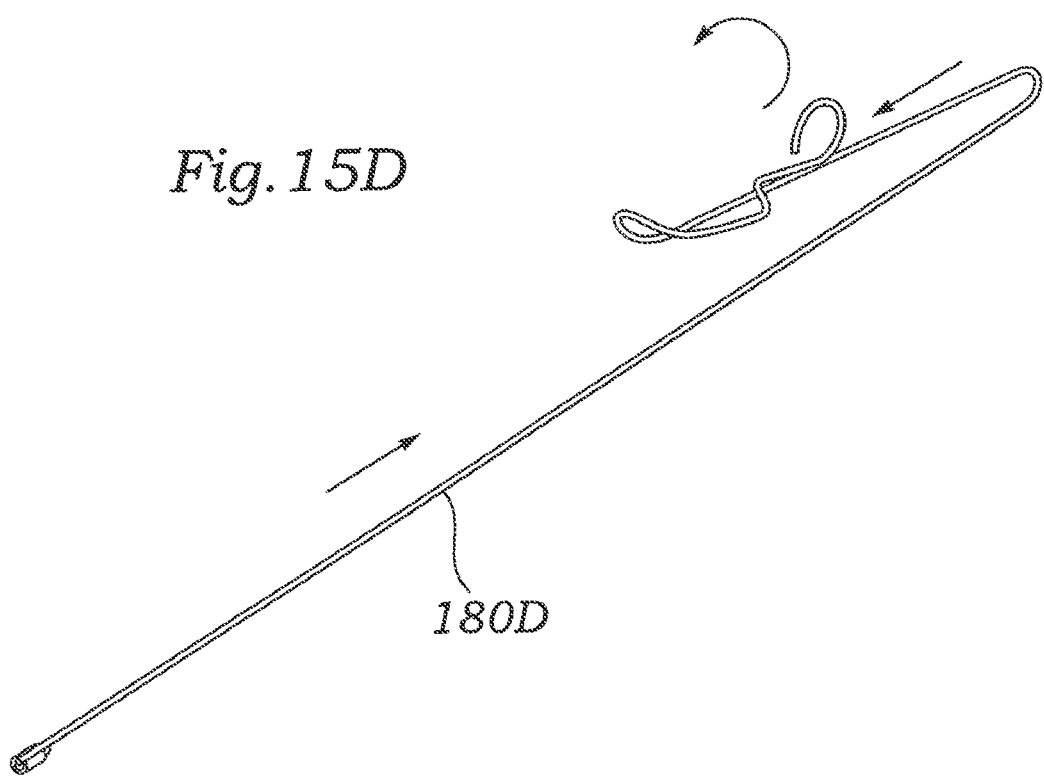
Figure 16:
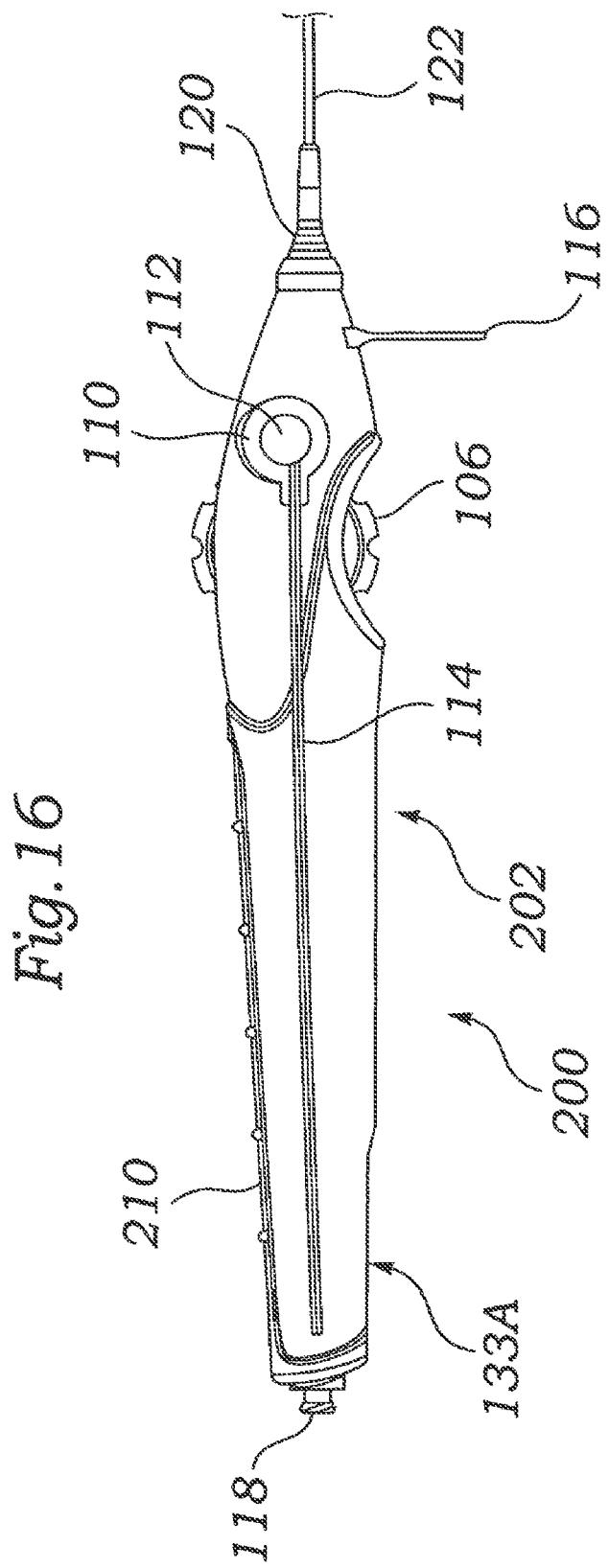
FIG. 16 illustrates side view of a delivery system according to the present invention.

FIG. 15D illustrates another example path of cord 180D which passes around fewer anchor members and therefore provides a ratio of user input to outer tubular member 124 movement close to 1:1. For comparison, FIG. 15D can be compared with FIGS. 2-5 to appreciate the path of the cord 180D. One end of the cord 180D is wrapped around the spool 154, then passes around stationary anchor member 150, through aperture 108A of the movable deployment lever 108, down around slider 152, then back to rear anchor 156 (seen best in FIG. 14).

The path of the cord 180 may be configured in a variety of other arrangements according to the present invention to achieve a desired retraction ratio. Typically, a retraction ratio that provides a slower retraction (e.g. 2 cm of deployment lever 106 movement to 1 cm of outer tubular member 124 movement) may be preferred for smaller stents (e.g. 20-90 mm), while a retraction ration that provides a quicker retraction (e.g. 1 cm of movement of deployment lever 108 to 1 cm of movement of outer tubular member 124) may be preferred for larger stents (e.g. 90-170 mm). However, it should be understood that most ratios can be used for any commonly used stents lengths, leaving the ratio as a matter of preference for the user.

While both the thumbwheel 106 and the deployment lever 106 act on the cord 180 to retract the slider 152, it should be appreciated that these two mechanisms act independently of each other and therefore do not affect the relative performance of the other. In other words, if the user switches between these two deployment controls, there will not be a "lag" as slack in the cord 180 is taken up by the second control. Instead, actuation of either deployment control maintains tension on the cord 180 so that movement of either deployment control will immediately move the slider 152. For example, if the deployment lever 108 is initially moved, the cord 180 maintains tension so that subsequent rotation of the thumbwheel 106 causes immediate movement of the slider 152.

By contrast, if the user initially pulls the rapid deployment ring 110, slack may be created in the cord 180. If either the thumbwheel 106 or the deployment lever 108 is then moved, that slack in the cord 180 will first be taken up by their movement, causing a delay in the retraction of the outer tubular member 124 until tension in the cord 180 increases. If a user, who cannot see these inner mechanisms or slack in the cord 180, is not expecting this delay, they may mistakenly think that the delivery system 100 is broken or has finished deploying the stent 160. Thus, the independent arrangement of the thumbwheel 106 and the deployment lever 108 provide a more consistent and predictable deployment procedure.

In operation, the inner tubular member 128 is fed over a guidewire and guided to a target location within the patient. Typically, radiopaque markers within the distal end of the delivery system 100 are viewed fluoroscopically to confirm that the inner tubular member 128 has achieved the desired location within the patient.

Once the user is satisfied that the delivery system 100 is in a desired position, the user actuates one of the three deployment controls. Typically, the outer tubular member 124 is retracted slowly at first, allowing the distal end of the stent 160 to expand or "flower" against the target tissue of the patient. While the user can initially retract the outer tubular member 124 with any of the three delivery controls, the thumbwheel 106 and the deployment lever 108 may allow for a slower and more controlled retraction since either can be controlled with only the user's thumb.

If the user desires to maintain a slow and highly controlled retraction of the outer tubular member 124, the thumbwheel 106 or deployment lever 108 use may be continued until the stent 160 has been completely uncovered and expanded against the target area. However, if the user desires to quickly retract the portion of the outer tubular member 124 that remains over the stent 160, the rapid deployment ring 110 can instead be used for more rapid retraction. The user simply pulls the rapid deployment ring 110 along slot 114 until the stent 160 has been fully deployed. Once the stent 160 has been fully deployed, the delivery device 100 is retracted from the patient, completing the delivery procedure.

It should be appreciated that any of the three deployment controls can be used by the user, alone or in various combinations, to retract the outer tubular member 124 and deliver the stent 160. While the use of the deployment controls may rest largely with the preference of the user, other factors may contribute to such a selection. For example, shorter stents (e.g. 20-90 mm) may be deployed more effectively with the precision of the thumbwheel 106 or deployment lever 108 while longer stents (e.g. 100-170 mm) may be more effectively deployed with a combination of the thumbwheel 106 initially and the rapid deployment ring 110 subsequently.

FIGS. 16-19 illustrate another preferred embodiment of a stent delivery system 200 according to the present invention. The stent delivery system 200 is similar to the previously discussed stent delivery system 100, but lacks the deployment lever 108, providing the user with only the thumbwheel 106 and rapid deployment ring 110 to retract the outer tubular member 124.

The stent delivery system 200 utilizes the same inner frame member 146 and body shell members 132A and 132B by including a cover plate 210 which is positioned over the rack 144 and over the sides of the inner frame member 146. The cover plate 210 blocks the aperture created by the body shell members 132A and 132B where the deployment lever 108 is positioned in the previously described delivery system 100.

Figure 17:
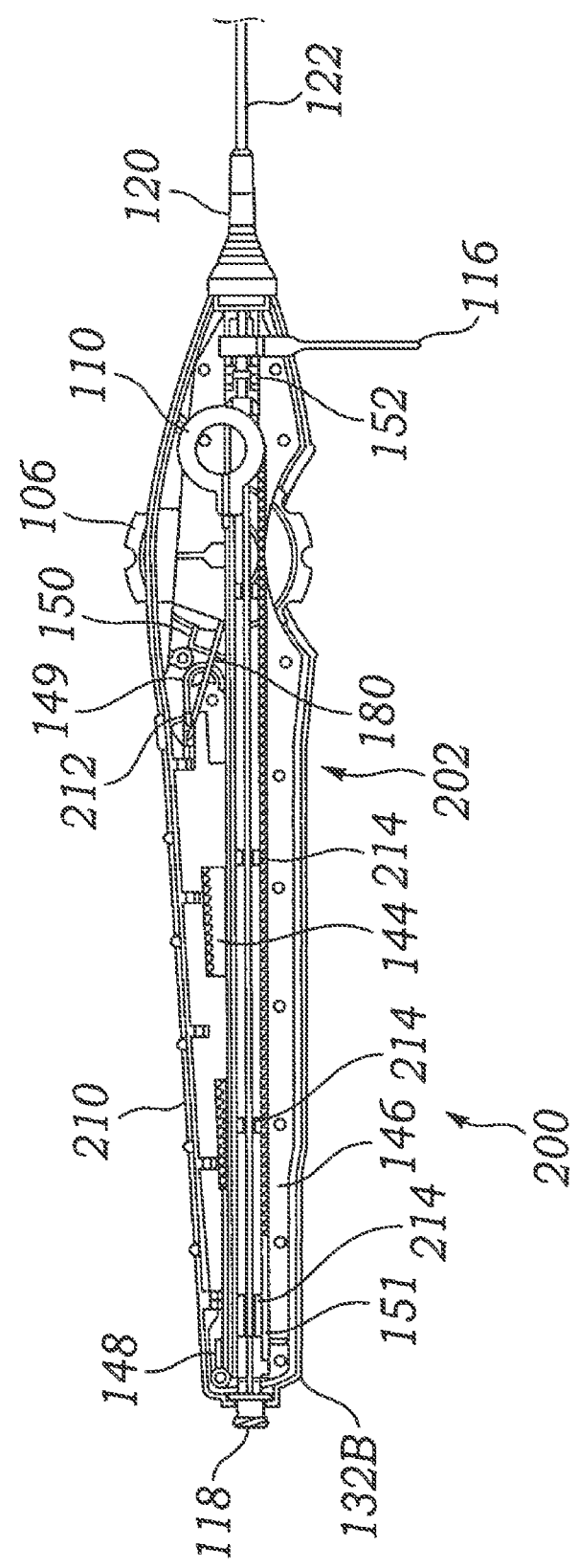
FIG. 17 illustrates a partially disassembled side view of the delivery system of FIG. 16.
Figure 18:
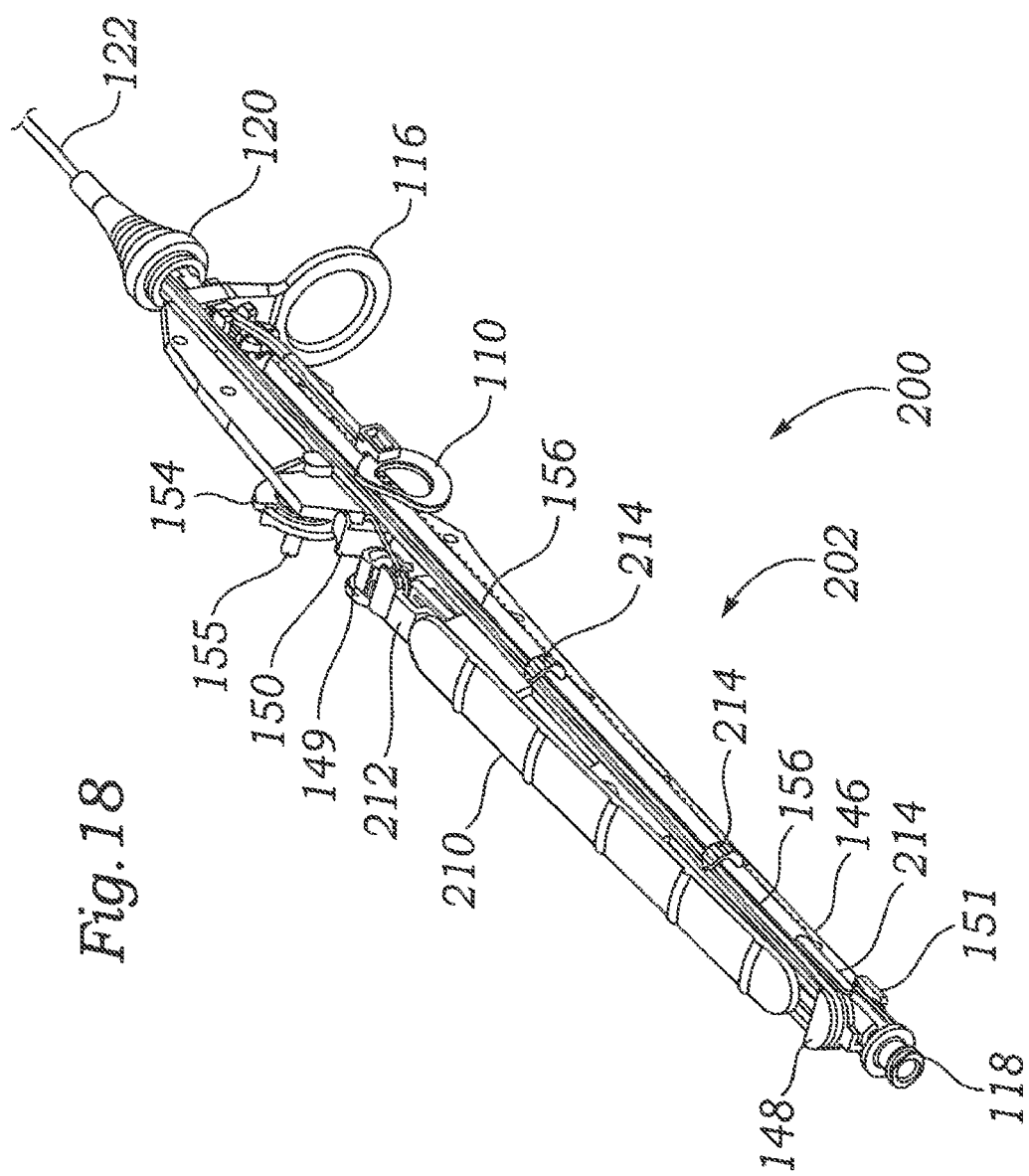
FIG. 18 illustrates a partially disassembled perspective view of the delivery system of FIG. 16.
Figure 19:
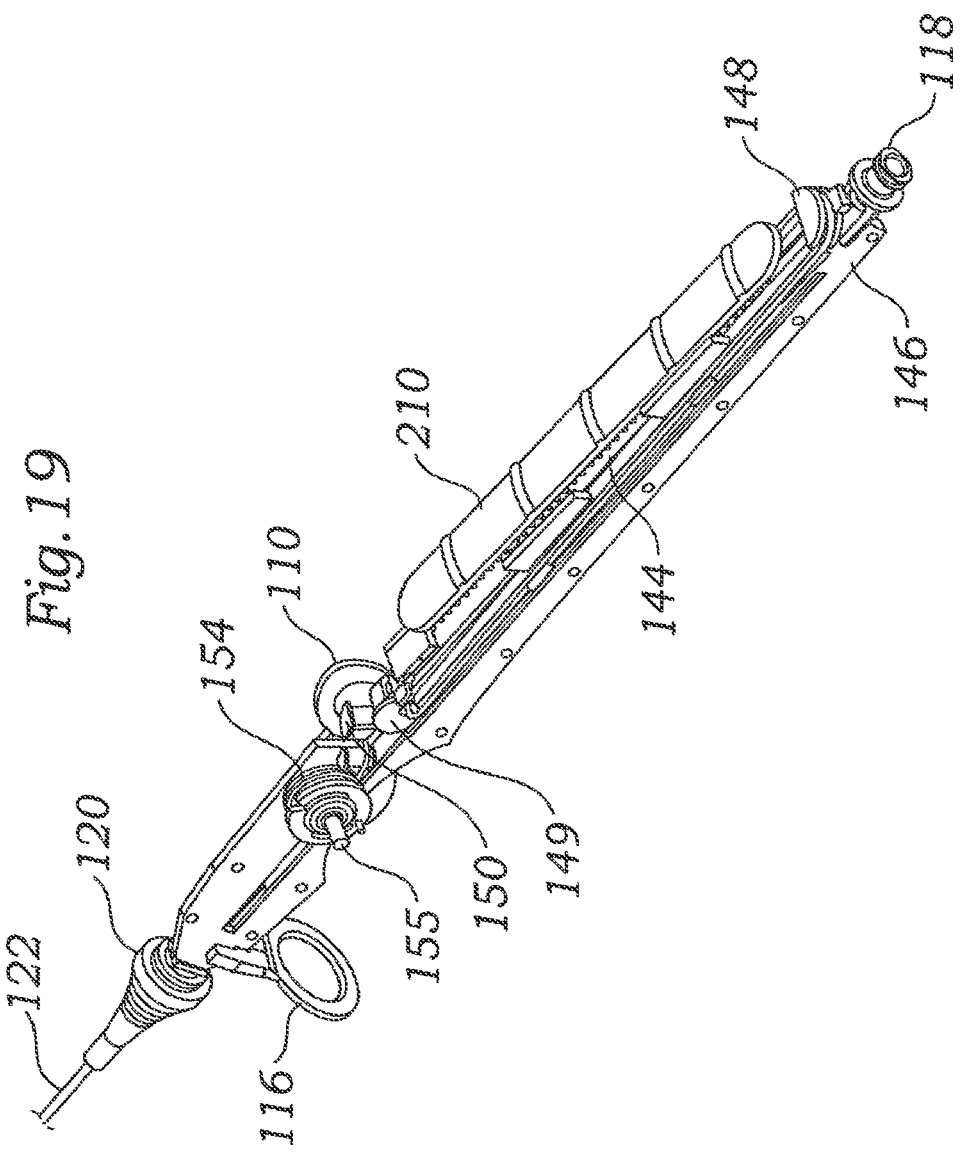
FIG. 19 illustrates a partially disassembled perspective view of the delivery system of FIG. 16.

Additionally, referring to FIGS. 17-19, the cover plate 210 includes an aperture 212 through which the cord 180 may be positioned. Since the deployment lever 108 is not present in this preferred embodiment, the aperture 212 provides a passage similar to passage 108A of the deployment lever 108. This aperture 212 allows the handle portion 202 to provide similar cord path configurations as those shown in FIGS. 11A-11D.

As best seen in FIGS. 17 and 18, the stent delivery system 200 also includes support blocks 214 that are attached to the inner frame member 146. The support blocks 214 form an aperture with the side of the inner frame member 146 which is positioned around rigid area 156 of the inner tubular member 128. The additional support provided to the rigid area 156 further reduces the likelihood that the rigid area 156 will bend or fold during retraction of the outer tubular member 124. This bending or folding can result from friction between the inner tubular member 128 and outer tubular member 124 during retraction of the slider 152. Additionally, these support blocks 214 can act as stops for the slider 152, preventing the outer tubular member 124 from being retracted any further.

It should be understood that different elements, assemblies, or aspects of each embodiment can be removed from, added to, or combined with other embodiments. For example, the support blocks 214 can be used with the stent delivery system 100. In another example, the preferred embodiment of FIG. 1 can include only the thumbwheel 106 and deployment lever 108, leaving off the rapid deployment ring 110. (This means that the deployment lever 108 may be moved into the area otherwise occupied by the rapid deployment ring. Additionally, a cover, similar to cover plate 210 can be used to cover an open area, allow the manufacture to use similar parts (e.g. similar outer body member 132A and 132B for each design).

While the stent delivery systems 100 and 200 have been primarily described as delivering stents, these embodiments may be modified to deliver other prosthesis devices that can be delivered within a retractable outer tubular member 124.

In some situations, a stentor other device must be delivered within a patient through a convoluted delivery path. As the path of the delivery device becomes more tortuous, the delivery device itself may become contorted. In such situations, the ability of the stability sheath 122 to transmit torque generated at the handle portion 102 may be reduced. In other words, a proximal end of the stability sheath 122 may twist without resulting in the same degree of twist to the distal end. In one example, the user attempts to rotate the handle portion 102 but the stability sheath 122 tends to "corkscrew" or twist and cause compression on the outer tubular member 124. In some circumstances, such a compression force can inhibit the outer tubular member 124 from retracting and therefore complicate stent deployment. In a worst case, such compression may result in tearing or other breakage of the delivery system, causing further complications.

Figure 20:
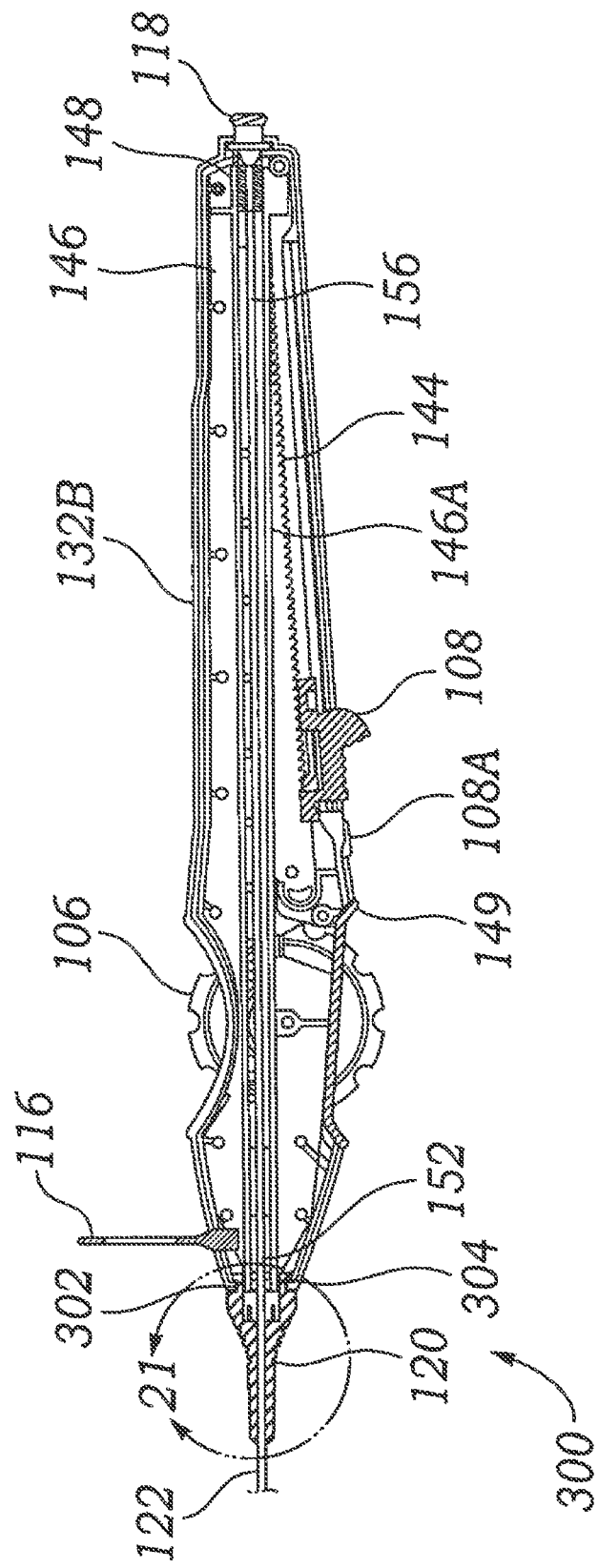
FIG. 20 illustrates a side cross section view of a preferred embodiment of a delivery system according to the present invention.
Figure 21:
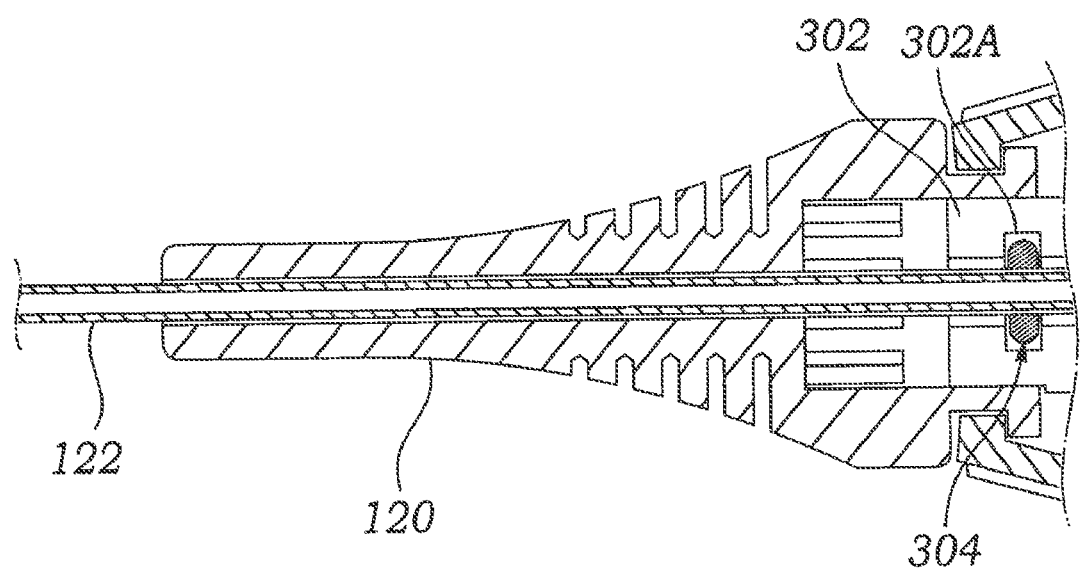
FIG. 21 illustrates a side cross section view of area 21 of FIG. 20.

FIGS. 20 and 21 illustrate another preferred embodiment of a stent delivery system 300 according to the present invention that seeks to eliminate the possibility of twisting by the stability sheath 122. Generally, the stent delivery system 300 is similar to the previously described delivery systems of this specification except that the stability sheath 122 is configured for rotation relative to the other elements of the system 300, and particularly relative to the handle 102 and outer tubular member 124. As a result, rotation of the handle portion 102 of the delivery system 300 can occur without requiring rotation of the stability sheath 122.

As seen best in FIG. 21, this rotational capability of the stability sheath 122 is preferably achieved by providing a circular disc member 304 near the proximal end of the stability sheath 122. This disc member 304 is positioned within a circular cavity 302A within a distal end 302 of the inner frame member 146. The circular cavity 302A is preferably slightly larger than the disc member 304 to allow for rotation of both the disc member 304 and the stability sheath 122 but not so large as to introduce an undesirable amount of "play" in which the disc member can move. The disc member 304 is preferably bonded to the stability sheath 122 or can alternately be integrally formed with the stability sheath 122. In this respect, the disc member 304 retains the axial position of the stability sheath 122 on the delivery device 300 while also allowing free rotation of the stability sheath 122.

Since the above-described configuration results in the independent rotation of the stability sheath 122 relative to the delivery system 300, it is desirable to minimize friction between the strain relief member 120 and the stability sheath 122. In this regard, a low friction coating may be applied to the inner passage of the strain relief member 120 and the outer surface of the stability sheath 122. Alternately, a lubricant may be introduced between these surfaces. Friction is also preferably minimized between the inner surface of the stability sheath 122 and the outer surface of the outer tubular member 124. This further facilitates independent rotation of the stability sheath 122.

In operation, the user advances the delivery portion 104 of the delivery device 300 into the patient and rotates the handle portion 102 to achieve a desired orientation of the delivery portion 104. As with previously described embodiments, the handle portion 102 and the delivery portion 104 are fixed relative to one another and thus rotation of the handle portion 102 will result in corresponding rotation of the delivery portion 104. However, due to the use of the circular disc member 304 described above, the stability sheath 122 is not forced to rotate along with the delivery portion 104 or handle portion 102. As a result the stability sheath 122 does not inadvertently inhibit (e.g., through compression, friction, etc.) the movement of the delivery portion 104 within the patient. Therefore complications during a delivery procedure are minimized.

Figure 22:
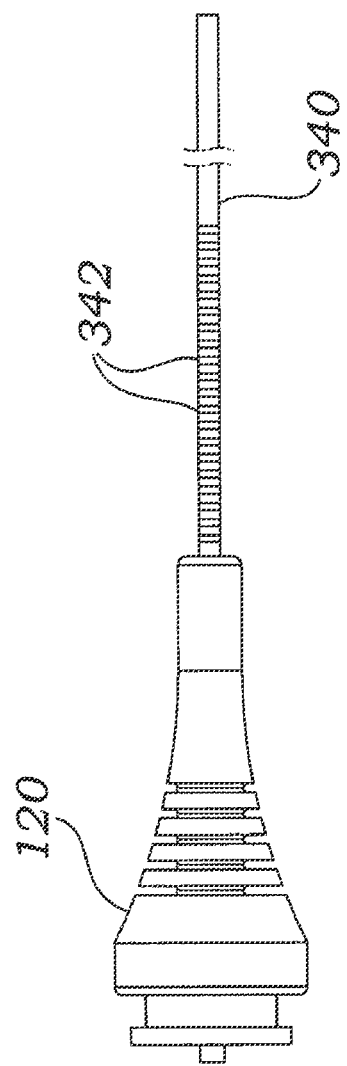
FIG. 22 illustrates a side view of a preferred embodiment of an axially compressible stability sheath according to the present invention.

FIG. 22 illustrates another preferred embodiment of a stent delivery system according to the present invention which seeks to reduce complications resulting from twisting by the stability sheath 340. While the preferred embodiment illustrated in FIGS. 20 and 21 seeks to prevent twisting, the present embodiment compensates for the effects of twisting by providing a region on the stability sheath 340 that compresses in length. This allows for a proximal end of the stability sheath 340 to remain secured to the handle portion 102 while allowing a distal end of the stability sheath 340 to axially retract along with the outer tubular member 124 if the two are frictionally engaged with one another.

The stability sheath 340 includes a plurality of circumferential crumple zones 342 located along a length of the sheath 340. Preferably, these crumple zones 342 are located near the proximal end of the sheath 340, just distal to the strain relief member 120. Each crumple zone 342 is configured to compress under axial pressure similar to an "accordion" region of a bendable straw. Therefore, if the stability sheath 340 becomes twisted and thereby frictionally engages the outer tubular member 124, the crumple zones 342 will compress in length when the user retracts the outer tubular member 124 (i.e., when the user retracts the outer tubular member 124 to deploy the stentor other prosthesis). In this respect, the crumple zones 342 allow the distal end of the stability sheath 340 to move with the outer tubular member 124 instead of otherwise preventing retraction.

Preferably, the crumple zones 342 allow a length of axial compression at least equal to the length of the prosthesis to be deployed. In other words, if the stability sheath 340 does bear down on the outer tubular member 124, the crumple zones 342 will allow the stability sheath 340 to move with the outer tubular member 124 until the prosthesis has been delivered.

Preferably, each of the crumple zones 342 compress in length by folding or buckling, similar to an accordion. In one example, this folding can be achieved by decreasing the thickness of each crumple zone 342 relative to the thickness of the surrounding portions of the stability sheath 340. When axial force is applied to the stability sheath 340 (i.e. by retraction of the outer tubular member 124), the weaker areas of the crumple zones 342 buckle, decreasing the overall length of the stability sheath 340.

Crumple zones 342 with decreased thicknesses can be created with various techniques known in the art. For example, the zones 342 can be formed as a unitary part of the stability sheath 340. Alternately, areas of decreased thicknesses can be cut out or otherwise removed with laser or mechanical cutting tools. In another example, the areas of decreased thickness can be created by adding additional layers of material around each crumple zone 342.

In another preferred embodiment, each of the crumple zones 342 can be created by introducing circumferential accordion-like creases along the stability sheath 340 (i.e. creases oriented inward and outward of the sheath 340 similar to a creased region of a bendable straw). In yet another preferred embodiment, the crumple zones 342 can be created with perforations or small punctures to weaken the stability sheath 340 and promote buckling.

In operation, the user advances the delivery portion 104 of the delivery device into the patient and rotates the handle portion 102 to achieve a desired orientation of the delivery portion 104. As with previously described embodiments, the handle portion 102 and the delivery portion 104 are fixed relative to one another and thus rotation of the handle portion 102 will result in corresponding rotation of the delivery portion 104. If such rotation results in the twisting of the stability sheath 340 on the outer tubular member 124, the crumple zones 342 will compress in length as the outer tubular member is retracted. As a result the stability sheath 340 does not inadvertently inhibit (e.g., through compression, friction, etc.) the movement of the delivery portion 104 within the patient. Therefore complications during a delivery procedure are minimized.

Another preferred embodiment according to the present invention seeks to eliminate twisting of the stability sheath 122 with a breakaway bond between the stability sheath 122 and the handle portion 102. Preferably, the sheath 122 and the handle portion 102 can be arranged similarly to the embodiments of FIGS. 1-19. However, a reduced amount of bonding material can be used to fix the stability sheath 122 to the frame member 146, allowing the stability sheath 122 to break free under pressure and move with the outer tubular member 124. The user can adjust the amount of "breakaway force" needed to break the stability sheath 340 free by varying the amount and type of adhesive or bonding agent.

As the user rotates the handle portion 102 during a delivery procedure the proximal end of the stability sheath 122 may twist relative to the distal end, creating force on the bond between the stability sheath 122 and the handle portion 102. As the force on the bond reaches a predetermined amount, it breaks, allowing the sheath 122 to either untwist under its own force or remain twisted and therefore move with the outer tubular member 124. In either scenario, the stability sheath 122 is prevented from inhibiting the movement of the outer tubular member 124 and therefore delivery of the prosthesis.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A stent delivery system, comprising:
a first tubular member having a distal end sized and shaped to receive a stent and a proximal end stiffer than the distal end;
a second tubular member being longitudinally slidable over said first tubular member;
a handle body;
a strain relief element coupled to a distal end of the handle body;
a third tubular member being at least partially disposed over said second tubular member, said third tubular member being longitudinally compressible relative to said first tubular member and to said second tubular member, extending distally of a distal end of the strain relief element, and coupled to the handle body;
wherein
the handle body is coupled to said second tubular member to retract said second tubular member relative to said first tubular member,
and
the strain relief element is at least partially disposed over the third tubular member.

2. The stent delivery system of claim 1 wherein the third tubular member comprises a stability sheath distal of the strain relief element.

3. The stent delivery system of claim 1 wherein stability sheath comprises a crumple zone.

* * * * *